(12) United States Patent
Bhatia et al.

(10) Patent No.: US 10,260,039 B2
(45) Date of Patent: Apr. 16, 2019

(54) MICROGELS AND MICROTISSUES FOR USE IN TISSUE ENGINEERING

(75) Inventors: Sangeeta N. Bhatia, Lexington, MA (US); Cheri Y. Li, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 398 days.

(21) Appl. No.: 14/116,901

(22) PCT Filed: May 11, 2012

(86) PCT No.: PCT/US2012/037656
§ 371 (c)(1),
(2), (4) Date: Apr. 14, 2014

(87) PCT Pub. No.: WO2012/155110
PCT Pub. Date: Nov. 15, 2012

(65) Prior Publication Data
US 2014/0212910 A1    Jul. 31, 2014

Related U.S. Application Data

(60) Provisional application No. 61/484,987, filed on May 11, 2011.

(51) Int. Cl.
*C12M 3/06* (2006.01)
*C12N 5/00* (2006.01)
*C12Q 1/02* (2006.01)
*C12N 5/071* (2010.01)

(52) U.S. Cl.
CPC ......... *C12N 5/0012* (2013.01); *C12N 5/0062* (2013.01); *C12N 5/0671* (2013.01); *C12Q 1/02* (2013.01); *C12M 23/16* (2013.01); *C12N 2513/00* (2013.01); *C12N 2531/00* (2013.01); *C12N 2533/30* (2013.01)

(58) Field of Classification Search
CPC .. C12N 5/0012; C12N 5/0062; C12N 5/0671; C12N 2513/00; C12N 2531/00; C12N 2533/30; C12Q 1/02; C12M 23/16
USPC ......................................... 435/29, 382; 425/5
See application file for complete search history.

(56) References Cited

U.S. PATENT DOCUMENTS

| | | |
|---|---|---|
| 2006/0258000 A1 | 11/2006 | Allen et al. |
| 2006/0270032 A1 | 11/2006 | Bhatia et al. |
| 2010/0099048 A1* | 4/2010 | Thomas ................. G03B 27/54 430/322 |

OTHER PUBLICATIONS

Panda et al. (2008). Stop-flow lithography to generate cell-laden microgel particles. Lab on a Chip, v8(7), 1056-1061.*
Tsang et al. Fabrication of 3D hepatic tissues by additive photopatterning of cellular hydrogels. FASEB J. (2007), v21, p. 790-801.*

(Continued)

*Primary Examiner* — Sean C. Barron
(74) *Attorney, Agent, or Firm* — Nelson Mullins Riley & Scarborough LLP; Amy E. Mandragouras, Esq.; Ariana D. Harris

(57) ABSTRACT

The present invention features microgels and microtissues for use in tissue engineering. Featured is a microencapsulation device for making microgels and/or microtissues via an emulsion technology. Also featured are methods of making higher ordered structures that mimic in vivo tissue structures. Methods of us are also featured.

18 Claims, 25 Drawing Sheets
Specification includes a Sequence Listing.

(56) References Cited

OTHER PUBLICATIONS

Berry, M.N., et al., "High-yield preparation of isolated rat liver parenchymal cells: a biochemical and fine structural study," J. Cell Biol., vol. 43(3), pp. 506-520 (1969).
Douglas, E. et al., "Self-assembled cellular microarrays patterned using DNA barcodes," Lab on a Chip, vol. 7(11), 7 pages (2007).
Gartner, Z. J., et al. "Programmed assembly of 3-dimensional microtissues with defined cellular connectivity" PNAS, vol. 106(12), pp. 4606-4610 (2009).
Hsiao, S. C., et al., "Direct Cell Surface Modification with DNA for the Capture of Primary Cells and the Investigation of Myotube Formation on Defined Patterns," Langmuir, vol. 25(12), pp. 6985-6991(2009).
International Preliminary Report on Patentability, PCT/US2012/037656, dated Nov. 12, 2013, 9 pages.
International Search Report and Written Opinion, PCT/US2012/037656, dated Oct. 17, 2012, 9 pages.
Kachouie, N. et al., "Directed assembly of cell-laden hydrogels for engineering functional tissues," Organogenesis, pp. 234-244 (2010) <URL:http://ukpmc.ac.uk/articles/PMC3055649 /pdf/org0604 0234. pdf> [retrieved on Oct. 2, 2012].
Li, C. et al. "DNA-templated assembly of droplet-derived PEG microtissues," Lab on a Chip, vol. 11(17), 9 pages ( 2011).
Valignat, M-P., et al., "Reversible self-assembly and directed assembly of DNA-linked micrometer-sized colloids," PNAS, vol. 1020(12), pp. 4225-4229 (2005).

\* cited by examiner

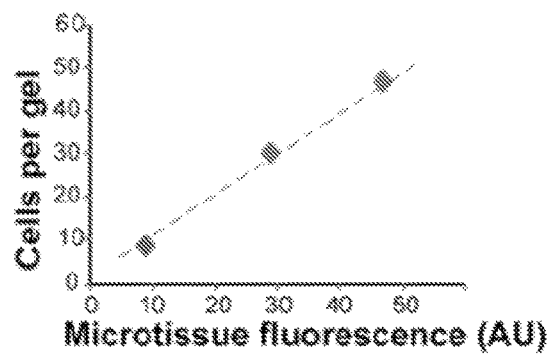
*Fig. 15A*
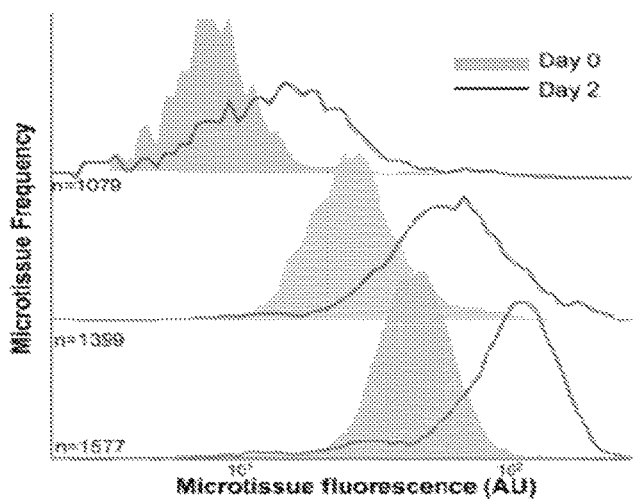
*Fig. 15B*
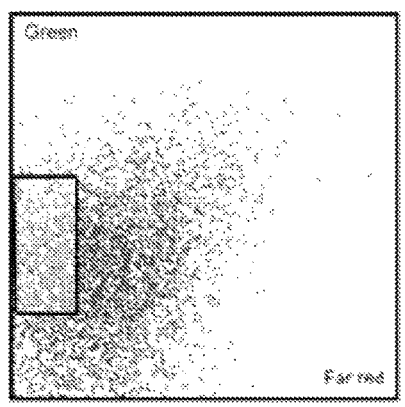 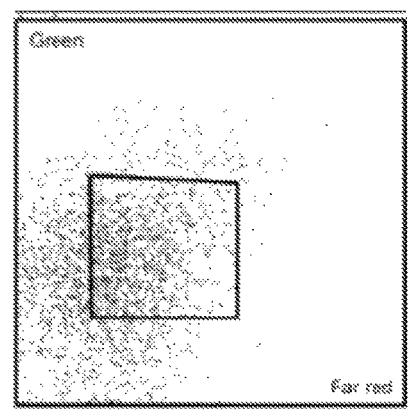
*Fig. 15C*     *Fig. 15D*

SEQUENCE LISTING

```
<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Arg Gly Asp Ser
1

<210> SEQ ID NO 2
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 2
aaaaaaaaaa gccgtcggtt caggtcata                                        29

<210> SEQ ID NO 3
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 3
aaaaaaaaaa atatgacctg aaccgacggc                                       30

<210> SEQ ID NO 4
<211> LENGTH: 30
<212> TYPE: DNA
<213> ORGANISM: Artificial Sequence
<220> FEATURE:
```

```
<223> OTHER INFORMATION: Synthetic oligonucleotide

<400> SEQUENCE: 4
aaaaaaaaaa agacacgaca cactggctta                                    30

<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 5
aaaaaaaaaa taagccagtg tgtcgtgtct                                    30

<210> SEQ ID NO 6
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 6
aaaaaaaaaa gcctcattga atcatgccta                                    30

<210> SEQ ID NO 7
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 7
aaaaaaaaaa taggcatgat tcaatgaggc                                    30

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 8
aaaaaaaaaa tagcgatagt agacgagtgc                                    30

<210> SEQ ID NO 9
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 9
aaaaaaaaaa gcactcgtct actatcgcta                                    30
```

MICROGELS AND MICROTISSUES FOR USE IN TISSUE ENGINEERING

RELATED APPLICATIONS

This application is a 35 U.S.C. 371 national stage filing of International Application No. PCT/US2012/037656, filed on May 11, 2012, which claims priority to and benefit of U.S. Provisional Application No. 61/484,987, filed May 11, 2011, the contents of each of which are hereby incorporated by reference herein.

STATEMENT OF FEDERALLY SPONSORED RESEARCH

This invention was made with government support under grant nos. ROI-DK56966 6914791 and ROI-EB008396 6920502, awarded by the National Institutes of Health (NIDDK). The government has certain rights in the invention."

SUMMARY OF THE INVENTION

The present invention features microgels and microtissues for use in tissue engineering. In particular the present invention features methods for fabricating polymerized hydrogels on a microscale. Microgels and/or microtissues of the present invention are capable of being assembled into larger ordered constructs which resemble or mimic in vivo tissue architecture. The microgels and/or microtissues of the invention are made using devices engineered to produce microscale droplets comprising living cells and/or other biologically relevant compounds wherein the droplets comprise, for example, a photopolymerizable hydrogel or other suitable scaffold component. During assembly, the droplets are made, mixed, and subsequently polymerized to form the microgels or microtissues of the invention. In preferred embodiments, the hydrogel components (or other scaffold components) are chemically modified or chemically modifiable in order to provide cell supportive or other assembly promoting properties. Microgels and/or microtissues of the present invention are particularly suitable for use in generating higher ordered structures. For example, the microgels and/or microtissues can be assembled on surfaces or substrates e.g., slides, tissue culture substrates, and the like, or can be assembled into larger three-dimensional structures for use in a variety of tissue engineering applications.

Described herein is an approach for the patterning and assembly of engineered tissues from microtissues, small units (<1 mm) of cell-laden hydrogels, programmed by the hybridization of single-stranded DNA oligonucleotides. Also described herein are approaches for the patterning and assembly of engineered tissues from microtissues in combination with microgels, e.g., microgels comprising biologically relevant compounds. Further described herein are alternative means for assembling the microtissues and/or microgels of the invention in order to create engineered tissues. This platform will have general utility for constructing in vitro disease models and commercial applications in biomedical tissue manufacture.

DETAILED DESCRIPTION OF THE INVENTION

Figure 1:
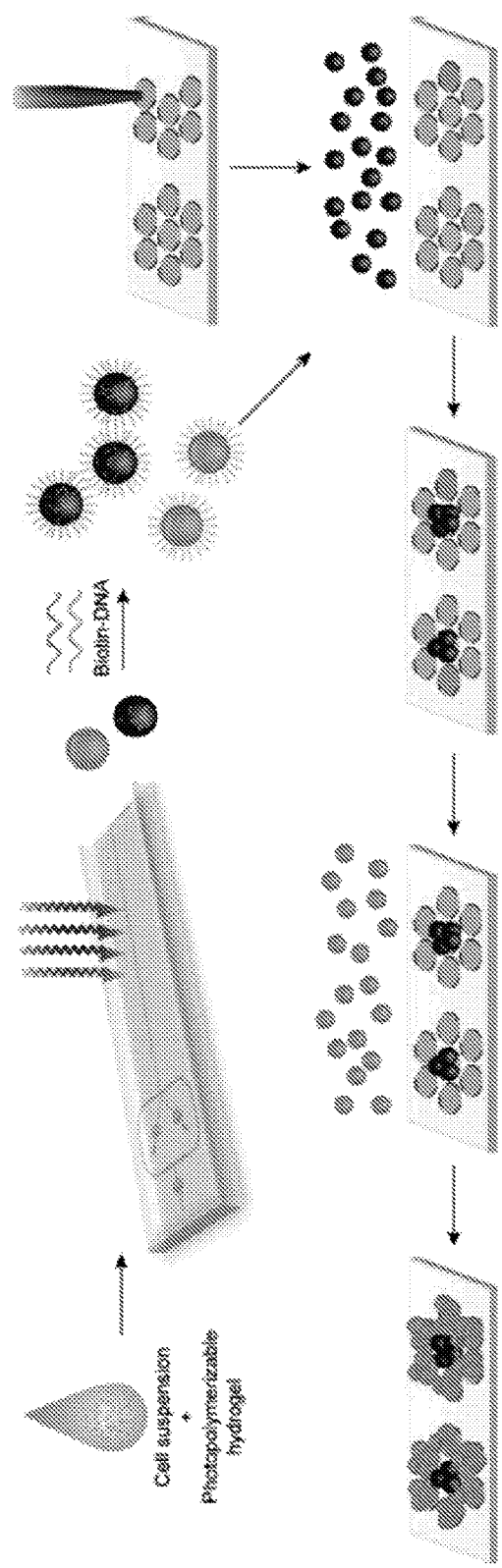
FIG. 1. Schematic of microtissue encapsulation, functionalization, and DNA-templated self assembly. Cells are injected with a photopolymerizable hydrogel prepolymer into a high-throughput microfluidic encapsulation device. Droplets of the cell-prepolymer mixture are exposed to UV on-chip to form streptavidin-containing microtissues which are then coated with 5'-biotin terminated oligonucleotides. Encoded microtissues containing different cell types are seeded on a DNA microarray template which directs the binding of microtissues to specific spots on the templating surface, attaining sequential DNA-templated patterning of cell-laden microtissues.

The invention provides methods of encapsulating cells or other biologically relevant molecules within microtissues or microgels on a microfluidic device, functionalizing the microtissues or microgels with an affinity ligand, e.g. with single-stranded DNA, and selectively binding microtissues (e.g., affinity ligand encoded, e.g., DNA encoded) to a variety of surfaces functionalized with the a complementary ligand (e.g., a templating ligand, e.g., complementary single-stranded DNA), including patterns on a templating slide or other hydrogels/microtissues. In exemplary aspects of the invention, cells are injected as a suspension in isopycnic medium into a cell encapsulation device. A photopolymerizable hydrogel, containing biotin-binding groups, is injected into the device simultaneously, and the two streams mix on-chip. The combined aqueous stream is then sheared by intersecting oil streams into uniform droplets, which are gelled through UV irradiation. Resulting microtissues are incubated with biotin-terminated single-stranded DNA to provide microtissue surfaces with specific recognition code. This code directs microtissue binding and assembly based on base-pair binding with complementary sequences.

In exemplary methods, encoded microtissues are assembled onto DNA-patterned templates, composed of microarrayed DNA spots on a glass slide. Encoded microtissues are seeded onto microarray slides, either in a concentrated slurry or by settling from a dilute suspension, and quickly bind (<10 minutes) to only target spots. Microtissues not bound to target spots are washed off, and the process is repeated with microtissues coated with other sequences (potentially containing different cell types, biomolecules, etc.) to sequentially build patterns of microtissue types. We further envision that DNA-directed assembly can be used to bind additional layers of microtissues upon this initial surface-templated layer.

Fundamentally, living tissues are composed of multiple cell types organized with microscale architectures. Current tools to specify heterostructures of cells include dielectrophoresis, molding (e.g. aggregates, cords), ECM-patterning, and DNA-modification of cells to direct assembly (Hsiao, S. C.; Shum, B. J.; Onoe, H.; Douglas, E. S.; Gartner, Z. J.; Mathies, R. A.; Bertozzi, C. R.; Francis, M. B. "Direct cell surface modification with DNA for the capture of primary cells and the investigation of myotube formation on defined patterns" *Langmuir* 2009, 25, 6985-6991. Gartner, Z. J.; Bertozzi, C. "Programmed assembly of three-dimensional microtissues with defined cellular connectivity" *Proc. Natl. Acad. Sci.* 2009, 106, 4606-4610). DNA-modified cells can be effectively assembled using orthogonal pairs of DNA-sequences, but the method has been demonstrated only for limited cell types. Furthermore, encoding DNA is bound directly onto cell membranes where covalently bound ligands may be susceptible to recycling and may potentially modify cell function. In general, current approaches focus on developing novel techniques to position individual cells, which can be then immobilized within a scaffold. This invention calls for a novel, inverse strategy of pre-encapsulating cells within a scaffold, and the subsequent positioning of these microtissues by DNA-hybridization.

Several non-obvious aspects of this invention address unique challenges in extending DNA-directed assembly from cells to microtissues. Until now, DNA-templated assembly has not been applied to larger units such as microtissues (100 um), which present inherent difficulties in mass transport (gravity becomes a dominant factor in the ability of surfaces to sufficiently interact) and binding (stronger washing forces on large objects require a larger number of DNA-hybridization bonds). To compensate the problem of increasing microtissue size, our method strictly controls the size of microtissues fabricated, and optimizes microtissue DNA-functionalization (using streptavidin-biotin binding) and template spotting to achieve high surface densities. Streptavidin-biotin based DNA-functionalization of microtissues is simple, modular, and cytocompatible.

Post-encoding of microtissues with biotin-DNA avoids UV damage that would occur by premixing DNA into the polymer, and allows the same batch of microtissues to be labeled after culture in various conditions. Other bioconjugation methods exist to modify hydrogel networks post-encapsulation (e.g. maleimide or NHS chemistries) but often require reaction conditions that are incompatible with maintaining the viability of encapsulated cells. Finally, the controlled spherical shape of droplet-derived microtissues minimizes contact area with templating surfaces, drastically reducing non-specific adhesion, and allowing templates to be made with a range of materials/chemistries (e.g. hydrophilic-glass vs. hydrophobic-PDMS). Spherical microtissues provide maximum surface area to volume for faster diffusion of nutrients to encapsulated cells, and can be assembled into isotropic structures (e.g. perfect close packing).

There are many advantages associated with patterning cellular microtissues rather than individual cells. First, cells are pre-encapsulated in a modular synthetic scaffold that can be easily customized with degradable linkages, adhesive ligands, and other biologically or chemically active factors. For sensitive cells such as primary hepatocytes, stabilization within a tailored 3D environment is necessary to promote their growth and function. Second, microtissues containing one cell type can be first cultured separately to stabilize homotypic interactions before they are assembled with other microtissues to activate heterotypic interactions. Third, because DNA is bound to the hydrogel scaffold rather than cell membranes, encoded microtissues can remain in assembled patterns for an extended period of time without additional measures for immobilization (e.g. embedding in agarose), and then removed for further culture, isolation, and biochemical analysis. These two advantages provide an additional layer of flexibility in studying the temporal aspects of intercellular signaling processes.

So that the invention may be more readily understood, certain terms are first defined.

As used herein, the term "microtissue" refers to a microscale polymerized hydrogel or other suitable scaffold which comprises living cells. As used herein, the term "microgel" refers to a microscale polymerized hydrogel or other suitable scaffold which comprises one or more biologically relevant compounds or agents. As used herein, the term microscale refers to objects having a size, e.g., a two-dimensional or three-dimensional feature size less than 1 mm. For example microscale objects can have a length and/or width and/or height and/or diameter or other feature size of greater than 1 µm and less than 1 mm. In preferred embodiments, microscale objects, e.g., microtissues and/or microgels of the invention have a size e.g., a diameter of 10 to 500 µm, 20 to 400 µm, 25 to 300 µm, or 50 to 250 µm.

As used herein the term "construct" refers to a higher ordered assembly of the microgels and/or microtissues of the invention. A construct can be assembled, for example, using the DNA directed assembly methods of the invention, using physical packing, or using other suitable chemical means of physically assembling the microgels and/or microtissues of the invention.

As used herein the term "on-chip emulsion" or "on-chip emulsification" refers to the generation of microtissues and/or micro gels of the invention using the physical devices, i.e., chips, defined herein.

As used herein, the term "co-culture" refers to a collection of cells cultured in a manner such that more than one population of cells are in association with each other. Co-cultures can made such that cells exhibit heterotypic interactions (i.e., interaction between cells of populations of different cell types), homotypic interactions (i.e., interaction between cells of the same cell types) or co-cultured to exhibit a specific and/or controlled combination of heterotypic and homotypic interactions between cells.

As used herein, the term "pre-mixing" refers to a mixing of cells and/or other biologically relevant components in a prepolymerized hydrogel or scaffold material in a manner such that components within the population are distributed, e.g., evenly distributed throughout the prepolymerized hydrogel or scaffold material.

As used herein, the term "encapsulation" refers to the confinement of a cell or population of cells within a material, in particular, within a biocompatible polymeric scaffold or hydrogel. The term "co-encapsulation" refers to encapsulation of more than one cell or cell type or population or populations of cells within the material, e.g., the polymeric scaffold or hydrogel.

As used herein, the term "biochemical factor" or "biochemical cue" refers to an agent of a chemical nature having a biological activity, for example, on a cell or in a tissue. Exemplary biochemical factors or cues include, but are not limited to growth factors, cytokines, nutrients, oxygen, proteins, polypeptides and peptides, for example, adhesion-promoting proteins, polypeptides and peptides, and the like. Exemplary adhesion-promoting peptides include those derived from the extracellular matrix (ECM) of a cell or tissue, including, but not limited to collagen-derived peptides, laminin-derived peptides, fibronectin-derived peptides (e.g., the RGD-peptides), and the like.

As used here in, the term "affinity biomolecules" refers to a biomolecule e.g., a protein, peptide, nucleic acid molecule, or the like, suitable for affinity binding to other compatible biomolecules. In exemplary embodiments of the invention, the affinity biomolecule is streptavidin in which is suitable for affinity binding to biotin. In other exemplary embodiments of the invention, the affinity biomolecule is a peptide, e.g., a cell adhesive peptide, suitable for affinity binding to compatible cell surface biomolecules.

Co-cultures can be maintained in vitro or can be included in engineered tissue constructs of the invention, maintained in vitro and/or implanted in vivo.

As used herein, the term "hydrogel" refers to a network of polymer chains that are hydrophilic in nature, such that the material absorbs a high volume of water or other aqueous solution. Hydrogels can include, for example, at least 70% v/v water, at least 80% v/v water, at least 90% v/v water, at least 95%, 96%, 97%, 98% and even 99% or greater v/v water (or other aqueous solution). Hydrogels can comprise natural or synthetic polymers, the polymeric network often featuring a high degree of crosslinking. Hydrogels also possess a degree of flexibility very similar to natural tissue, due to their significant water content. Hydrogel are particularly useful in tissue engineering applications of the invention as scaffolds for culturing cells. In preferred embodiments of the invention, the hydrogels are made of biocompatible polymers. Hydrogels of the invention can be biodegradable or non-biodegradable.

As used here, the term "parenchymal cells" refers to cells of, or derived from, the parenchyma of an organ or gland, e.g., a mammalian organ or gland. The parenchyma of an organ or gland is the functional tissue of the organ or gland, as distinguished from surrounding or supporting or connective tissue. As such, parenchymal cells are attributed with carrying out the particular function, or functions, of the organ or gland, often referred to in the art as "tissue-specific" function. Parenchymal cells include, but are not limited to, hepatocytes, pancreatic cells (alpha, beta, gamma, delta), myocytes, e.g., smooth muscle cells, cardiac myocytes, and the like, enterocytes, renal epithelial cells and other kidney cells, brain cell (neurons, astrocytes, glia cells), respiratory epithelial cells, stem cells, and blood cells (e.g., erythrocytes and lymphocytes), adult and embryonic stem cells, blood-brain barrier cells, adipocytes, splenocytes, osteoblasts, osteoclasts, and other parenchymal cell types known in the art. Because parenchymal cells are responsible for tissue-specific function, parenchymal cells express or secrete certain tissue specific markers.

Certain precursor cells can also be included as "parenchymal cells", in particular, if they are committed to becoming the more differentiated cells described above, for example, liver progenitor cells, oval cells, adipocytes, osteoblasts, osteoclasts, myoblasts, stem cells (e.g., embryonic stem cells, hematopoietic stem cells, mesenchymal stem cells, endothelial stem cells, and the like. In some embodiments stem cells can be encapsulated and/or implanted under specified conditions such that they are induced to differentiate into a desired parenchymal cell type, for example, in the construct and/or in vivo. It is also contemplated that parenchymal cells derived from cell lines can be used in the methodologies of the invention.

The term "non-parenchymal cells" as used herein, refers to the cells of or derived from the tissue surrounding or supporting parenchymal tissue in an organ or gland, for example, in a mammalian (e.g., human) organ or gland, or the connective tissue of such an organ or gland. Exemplary non-parenchymal cells include, but are not limited to, stromal cells (e.g., fibroblasts), endothelial cells, stellate cells, cholangiocytes (bile duct cells), Kupffer cells, pit cells, and the like. The choice of non-parenchymal cells used in the constructs of the invention will depend upon the parenchymal cell types used.

As used herein and in the appended claims, the singular forms "a," "and," and "the" include plural referents unless the context clearly dictates otherwise. Thus, for example, reference to "a cellular island" includes a plurality of such cellular islands and reference to "the cell" includes reference to one or more cells known to those skilled in the art, and so forth.

As used herein the term "encoding biomolecule" of "encoding affinity ligand" refers to an affinity biomolecules Incorporated within. or on the surface of, a microgel or microtissue of the invention. The term "templating biomolecule" or "templating affinity ligand" refers to affinity biomolecules, e.g. complementary affinity biomolecules, incorporated on the surface of a substrate, e.g. a cell culture or tissue culture substrate. As used herein the term "encoding DNA" refers to DNA incorporated within or on the surface of microgel or microtissue of the invention. The term "templating DNA" refers to DNA e.g., complimentary DNA Incorporated on the surface of a substrate e.g. a cell culture or tissue culture substrate.

Various aspects of the invention are described in further detail in the following subsections.

I. Cell Sources

The technology of the instant invention is readily amenable to use with a variety of cell types including primary cells, cell lines, transformed cells, precursor and/or stem cells, and the like. Exemplary embodiments feature use of parenchymal cells, optionally in combination with non-parenchymal cells, to produce engineered tissue constructs having differentiated function, e.g., for the modeling of primary tissues.

Parenchymal cells can be obtained from a variety of sources including, but not limited to, liver, skin, pancreas, neuronal tissue, muscle, and the like. Parenchymal cells can be obtained from parenchymal tissue using any one of a host of art-described methods for isolating cells from a biological sample, e.g., a human biological sample. Parenchymal cells. e.g., human parenchymal cells, can be obtained by biopsy or from cadaver tissue. In certain embodiments, parenchymal cells are derived from lung, kidney, nerve, heart, fat, bone, muscle, thymus, salivary gland, pancreas, adrenal, spleen, gall bladder, liver, thyroid, parathyroid, small intestine, uterus, ovary, bladder, skin, testes, prostate, or mammary gland.

In exemplary aspects, the invention employs constructs containing human parenchymal cells optimized to maintain the appropriate morphology, phenotype and cellular function conducive to use in the methods of the invention. Primary human parenchymal cells can be isolated and/or pre-cultured under conditions optimized to ensure that the parenchymal cells of choice initially have the desired morphology, phenotype and cellular function and, thus, are poised to maintain said morphology, phenotype and/or function in the constructs, and in vivo upon implantation to create the humanized animals of the invention Cells useful in the methods of the disclosure are available from a number of sources including commercial sources. For example, hepatocytes may be isolated by conventional methods (Berry and Friend, 1969, J. Cell Biol. 43:506-520) which can be adapted for human liver biopsy or autopsy material. In general, cells may be obtained by perfusion methods or other methods known in the art, such as those described in U.S. Pat. Pub. No. 20060270032.

Parenchymal and non-parenchymal cell types that can be used in the above-described constructs include, but are not limited to, hepatocytes, pancreatic cells (alpha, beta, gamma, delta), myocytes, enterocytes, renal epithelial cells and other kidney cells, brain cell (neurons, astrocytes, glia), respiratory epithelium, stem cells, and blood cells (e.g., erythrocytes and lymphocytes), adult and embryonic stem cells, blood-brain barrier cells, and other parenchymal cell types known in the art, fibroblasts, endothelial cells, and other non-parenchymal cell types known in the art.

Typically, in practicing the methods of the disclosure, the cells are mammalian cells, although the cells may be from two different species (e.g., humans, mice, rats, primates, pigs, and the like). The cells can be primary cells, or they may be derived from an established cell-line. Cells can be from multiple donor types, can be progenitor cells, tumor cells, and the like. In preferred embodiments, the cells are freshly isolated cells (for example, encapsulated within 24 hours of isolation), e.g., freshly isolated cells from donor organs. In certain embodiments, the cells are isolated from individual donor organs and an assembled tissue construct is specific for that donor. Any combination of cell types that promotes maintenance of differentiated function of the parenchymal cells can be used in the methods and constructs of the invention (e.g., parenchymal and one or more populations of non-parenchymal cells, e.g., stromal cells). Parenchymal cells which may be cultured in the constructs as described herein may be from any source known in the art, e.g., primary hepatocytes, progenitor-derived, ES-derived, induced pluripotent stem cells (iPS-derived), etc.

Further cell types which may be cultured in the constructs of the invention include pancreatic cells (alpha, beta, gamma, delta), enterocytes, renal epithelial cells, astrocytes, muscle cells, brain cells, neurons, glia cells, respiratory epithelial cells, lymphocytes, erythrocytes, blood-brain barrier cells, kidney cells, cancer cells, normal or transformed fibroblasts, liver progenitor cells, oval cells, adipocytes, osteoblasts, osteoclasts, myoblasts, beta-pancreatic islets cells, stem cells (e.g., embryonic stem cells, hematopoietic stem cells, mesenchymal stem cells, endothelial stem cells, etc.), cells described in U.S. patent application Ser. No. 10/547,057 paragraphs 0066-0075 which is incorporated herein by reference, myocytes, keratinocytes, and indeed any cell type that adheres to a substrate.

It is understood that constructs of the invention may contain parenchymal cells with one, or two or more types of non-parenchymal cells such as, for example, stromal cells, endothelial cells, etc. One of skill in the art will appreciate that particular patterns of non-parenchymal cells and/or parenchymal cells may be desired in some cases, e.g., when it is desired to mimic certain in vivo environments. It is understood that any support or accessory cells may be included in the constructs of the invention.

In other exemplary embodiments, the microtissues of the invention feature immortalized, transformed tumorgenic cells. Cells can be either primary cells, for example, from a tumor biopsy, or cell lines. In one embodiment, tumor cells are encapsulated within a first population of microtissues and stromal cells are encapsulated in a second population of microtissues. One or more populations of microtissues can further include, for example, ECM proteins entrapped therein. Alternatively, ECM components can be entrapped within separate populations or within a separate population of microgels. Higher ordered structures can be created using any combination or these microtissues or microgels.

II Device

Microencapsulation devices of the invention are described in detail in the appended Examples and Figures. In a preferred embodiment, a microencapsulation device on the invention comprises one or more injection ports in contact with a microchannel comprised therein, said injection ports for introducing one or more aqueous solutions, a droplet generating nozzle into which said solutions flow, an emulsion stream in contact with said droplet generating nozzle, a mixer section for dispersing components of droplets, a polymerizing section, and an outlet.

A preferred microencapsulation device is depicted in FIG. 2. The microencapsulation device includes two aqueous input ports into which aqueous solutions enter and streams are dispersed by shear flow from an oil stream into droplets that mix and travel down the UV-exposure channel, comprised in the polymerization section. In an exemplary embodiment, prepolymer (2× concentrated) and a cell suspension meet and flow into a 60 µm droplet generating nozzle. Vertical columns on either side of the channel provide visual references (50-100 µm below, 100-150 µm above) for real-time adjustment of droplet size. Droplets pass through a mixer section, e.g., a bumpy serpentine mixer section, to thoroughly disperse cells in prepolymer which are then polymerized by UV irradiation from a curing lamp, in the polymerization section. Microtissues are collected from the device (6000/min) via an outlet and are spherical and monodisperse. Microtissue size is controlled by the relative flow rates of the combined aqueous phase ($Q_P$) and the continuous oil phase ($Q_O$), and increases with prepolymer:oil flow ratio. Adding small amounts of a surfactant, e.g., Krytox 157 FSH fluorosurfactant into the oil decreased droplet diameter at all flow ratios, allows for higher prepolymer flow rates for a given microtissue size.

III Methods of Making Microtissues of Microgels

The present invention features processes by which to encapsulate cells and/or other biologically relevant components in microtissues or microgels. Cells or components are uniformly dispersed within prepolymerized hydrogel using "on-chip" emulsification, for example, using the microencapsulation device described herein. In preferred embodiments, cells are injected through a first inlet and prepolymer solution through a second inlet. Cells and prepolymer solution are allowed to come into contact (combined aqueous phase) and flow into a droplet generating nozzle. The combined aqueous phase is allowed to come into contact with the oil (continuous oil phase.) Speed of flow (flow rate) and/or nozzle size and/or nozzle shape control droplet size. Droplets pass through a mixing region of the channel within the device to disperse cells within prepolymer. Droplets then pass, in preferred embodiments, through a UV irradiation region of the channel or device (e.g., a portion of the device in contact with a UV source, e.g., a curing lamp. Microtissue size is controlled by the relative flow rates of the combined aqueous phase (QP) and the continuous oil phase (QO), and increases with prepolymer:oil flow ratio. Microtissues are collected from an outlet of the device.

This technique is referred to herein as "on-chip" emulsion or "on-chip" emulsification.

In the absence of an encapsulation device as described above, photo masking techniques can be used to generate microscale patterns, e.g., exposed substrate patterned in miscoscale spots using photomasking techniques. The skilled artisan, however, will appreciate the enhanced efficiency of the microencapsulation device technology.

The above described technology can likewise be used to generate microgels, by replacing cells with other biologically relevant compounds, e.g., ECM proteins, etc.

A preferred process features the use of a photopolymerizable hydrogel, e.g., a photopolymerizable PEG-based hydrogel. Other suitable hydrogels for use in the invention include, but are not limited to, alginates and the like. While these hydrogels are not photopolymerizable, they are amenable to chemical modification and can be cross-linked via alternative means (e.g., ionic crosslinking) in an emulsion. Preferably, hydrogels are biocompatible.

In exemplary embodiments, the hydrogel is functionalized for cell support and/or assembly purposes. Such scaffolds are also referred to as chemically modulatable scaffolds. For example, scaffolds can be modulated to include streptavidin, biotin, DNA, ECM peptides (e.g., RGD peptides) and the like, also referred to herein as "affinity biomolecules." In certain embodiments, conjugation of an "affinity biomolecule" is accomplished via incorporation of a modified polymer chain, e.g., an acrylate modified or conjugated chain. Preferably, affinity biomolecules or other functional groups for later attachment of biomolecules are incorporated into polymeric hydrogels in a manner such that they are accessible on the surface of microgels and/or micro tissues of the invention.

In some embodiments, cells and prepolymer can be mixed off chip, for example, where cells and prepolymer are compatible, e.g., cells (or biomolecules) are not adversely affected by longer association with prepolymer. In such embodiments, only a single aqueous stream is caused to contact the oil stream.

In certain embodiments, the microgels or microtissues are engineered to include one or more adherence materials to facilitate maintenance of the desired phenotype of the encapsulated cells. The term "adherence material" is a material incorporated into a construct of the invention to which a cell or microorganism has some affinity, such as a binding agent. The material can be incorporated, for example, into a hydrogel prior to seeding with parenchymal and/or non-parenchymal cells. The material and a cell or microorganism interact through any means including, for example, electrostatic or hydrophobic interactions, covalent binding or ionic attachment. The material may include, but is not limited to, antibodies, proteins, peptides, nucleic acids, peptide aptamers, nucleic acid aptamers, sugars, proteoglycans, or cellular receptors.

The type of adherence material(s) (e.g., ECM materials, sugars, proteoglycans etc.) will be determined, in part, by the cell type or types to be cultured. ECM molecules found in the parenchymal cell's native microenvironment are useful in maintaining the function of both primary cells and precursor cells and/or cell lines. Exemplary ECM molecules include, but are not limited to collagen I, collagen III, collagen IV, laminin, and fibronectin.

Preferred microtissues are on the order of 50 to 250 µm and comprise about 5-10 cells per microtissues. Viability of cells throughout microtissues can be monitored via conventional means. The microtissues of the invention have been demonstrated to have good viability and a relatively good distribution of cells throughout a population of particles.

Certain cells, e.g., tumor cells, can proliferate within microtissues of the invention, as well, providing additional functionality of the microtissues of the invention.

IV. Methods of Assembling Microtissues or Microgels.

Microtissues and/or microgels of the invention are readily assembled into higher ordered structures, for example, structures mimicking in vivo tissue architecture. In exemplary embodiments, microtissues and/or microgels are engineered to include an encoding biomolecule or affinity ligand and substrates, e.g., cell or tissue culture substrates, are patterned with a templating biomolecule or affinity ligand (e.g., a binding partner of the encoding biomolecule or affinity ligand.) The encoding biomolecule tells the microtissues and/or microgels what specific templating biomolecule or ligand to look for. The templating biomolecule or ligand attracts the complementary microtissues and/or microgels having encoding biomolecule or ligand within or on the surface. In this manner, one can make organized tissues, i.e., can organize microtissues and/or microgels in a pre-specified pattern.

In some embodiments, further 3D structure is obtainable, for example, by layering additional cells, for example of a different cell type, on top of already patterned microtissues and/or microgels. Moreover, even when patterned in an essentially 2D pattern, e.g., on a surface, cells within microtissues of the invention behave as if patterned in 3D, i.e., the cells behave as if having a 3D architecture based on the microtissue structure.

The Examples herein demonstrate the use of DNA as an encoding and/or templating biomolecule. Other means of patterning are envisioned, e.g., biotin or biotin conjugated biomolecules and complementary streptavidin or streptavidin-conjugated biomolecules. Cells themselves can also be used to attract certain microtissues and/or microgels of the invention in the assembly process. For example, cell attachment peptides (e.g., RGD) in one population of microtissues and/or microgels can attract cells and said cells can attract and bind other microtissues and/or microgels comprising cell attachment peptides.

An advantage of the technology of the instant invention is that any particular cell type can be optimized for function in a separate population of microtissues prior to assembly into higher ordered structures. Cells needing longer time in culture, specific nutrients, etc. can be maintained in one population of microtissues and cells having distinct requirements in a second population of microtissues. Subsequent assembly enjoys the advantage of each cell type being in optimal condition when patterned.

Assembly can also be via physical means. For instance, microtissues and/or microgels of the invention can be physically trapped or contained in a vessel or structure, e.g., on a chip, slide, microchamber, etc. In a preferred embodiment, microtissues are contained within a microfluidic chip or device. Width of channels within the chip or device can be altered to control assembly. A filter can be included at one or more outlets of the microfluidic chamber to retain microtissues and/or microgels. Wider channels can accommodate the flow of microtissues and/or microgels into chips or devices. Channels can also accommodate media or other aqueous flow around microtissues and/or microgels. In exemplary embodiments, microtissues containing hepatocytes are assembled in microfluidic chips or devices. Aqueous solutions or media can include test compounds, e.g., test drugs, etc. Metabolism of such compounds can further be tested, e.g., in eluate from the microfluidic chip or device.

Cells within microtissues, e.g., hepatic cells, can metabolize compounds in the media or respond to compounds in the media (media or solution.) In further embodiments, cells from higher ordered structures can be samples or "biopsied" post treatment with compound to determine the effect of said compound on the tissue.

Cells within microtissues, e.g., tumor cells can be tested for response to compounds, e.g., tested for their proliferative response to compounds. Microtissue sorting can be utilized to determine proliferative response, or inhibition of proliferation, as described herein.

Trans-well-like devices are also envisioned for use in the instant invention to assemble microtissues and/or microgels. Trans-wells are devices designed to be inserted into cell culture ware, e.g., into the wells of culture dishes or multi-well plates. Trans-well-like devices can have altered membrane properties, e.g., larger pore sizes, to facilitate media flow to microtissues and/or microgels but retain microtissues and/or microgels.

It is also envisioned that one chip designed to mimic one in vivo tissue could be integrated with one or more additional chips mimicking other tissues to generate an "organ on a chip" or "organism on a chip."

V. Uses

The methodology and constructs of the invention are useful in a number of different methods as set forth in more detail below.

This platform technology is anticipated to have utility in the development of engineered tissues for basic research, human therapies, drug development, drug testing, and disease models. It is proposed that this technology will be particularly useful for enabling higher fidelity construction of complex engineered tissue model systems such as liver and other highly differentiated and complex tissues, which are notably the tissue-types most relevant for drug toxicity screening by pharmaceutical companies (e.g., for testing novel compounds for biocompatibility). Additionally, it is envisioned that this platform to be useful in basic science research. Specifically, the engineered constructs can serve as model systems for studying 3D cell-cell interactions in diverse fields ranging from stem cell to cancer biology. The rapid and facile construction of microgels and microtissues, including higher ordered assemblies of these micro tissues and/or microgels, using the devices and methodologies described herein enables complex, organized cellular 3D patterning to be combined with a variety of screening applications (e.g., genetic model systems, toxicology screens, etc.). In summary, this technology allows studies of engineered tissues and cellular model systems of both complexity and scale that are precluded by current technologies and methods.

The methodology of the invention is particularly suited for use in basic research, modeling disease states, testing potential drug compounds in vivo, toxicology screening, and the like. In exemplary embodiments, the invention features constructs in which cells are patterned to achieve a high degree of similarity to a chosen in vivo system. For example, constructs featuring parenchymal cells or highly differentiated cells can be patterned to mimic the physiologic properties of the corresponding or source tissue from which the cells are derived. In certain embodiments, the function of parenchymal or highly differentiated cells is enhanced in constructs of the invention by choosing particular combinations of parenchymal and/or non-parenchymal cells, for example, parenchymal cells and stromal cells (e.g., fibroblasts.) Combinations of cells can be patterned at distinct locations within the constructs of the invention and/or within adjacent locations within the constructs (e.g., to facilitate cell-cell communication between distinct cell types.) In exemplary embodiments, the constructs feature cell populations patterned to mimic interactions between cells involved in the organization of tissues in vivo.

The methodology of the instant invention provides for the generation of 3D microtissue-based "miniature" organs on a chip. In exemplary embodiments, the invention provides for the generation of 3D microtissue-based "miniature" liver on a chip (e.g. for metabolism, drug response or disease modeling). Primary hepatocytes are encapsulated in 3D within, for example, PEG material, along with co-encapsulated cell types or signals needed to stabilize their function. Miniaturized versions of these 3D gels (FIG. 12) can be packed into a microfluidic chamber (like a packed bed reactor) and media can be perfused through the interstitial spaces between the gels.

Figure 13:
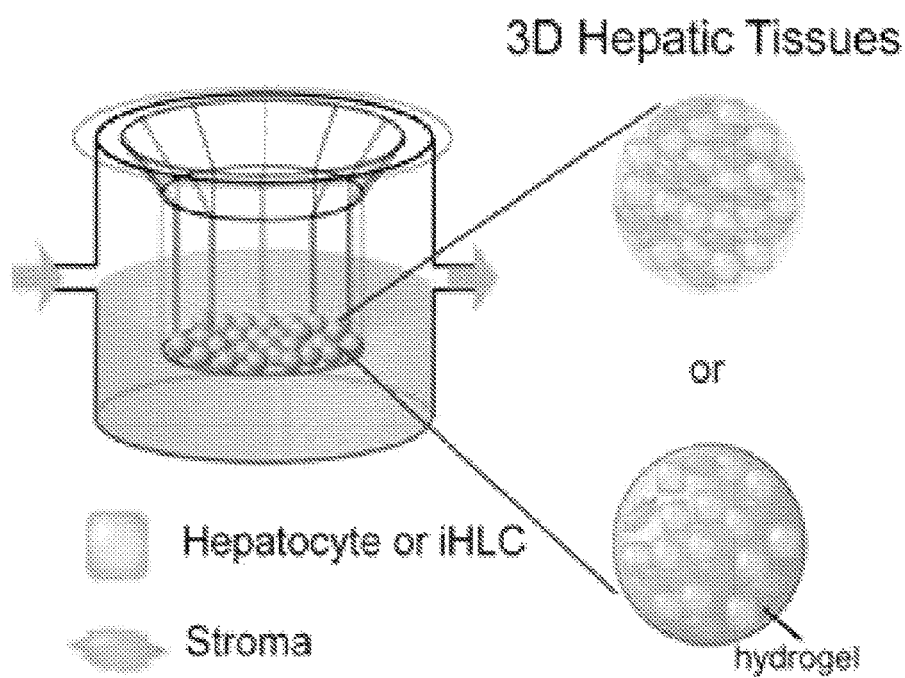
FIG. 13. Membrane perfusion format.
Figure 14:
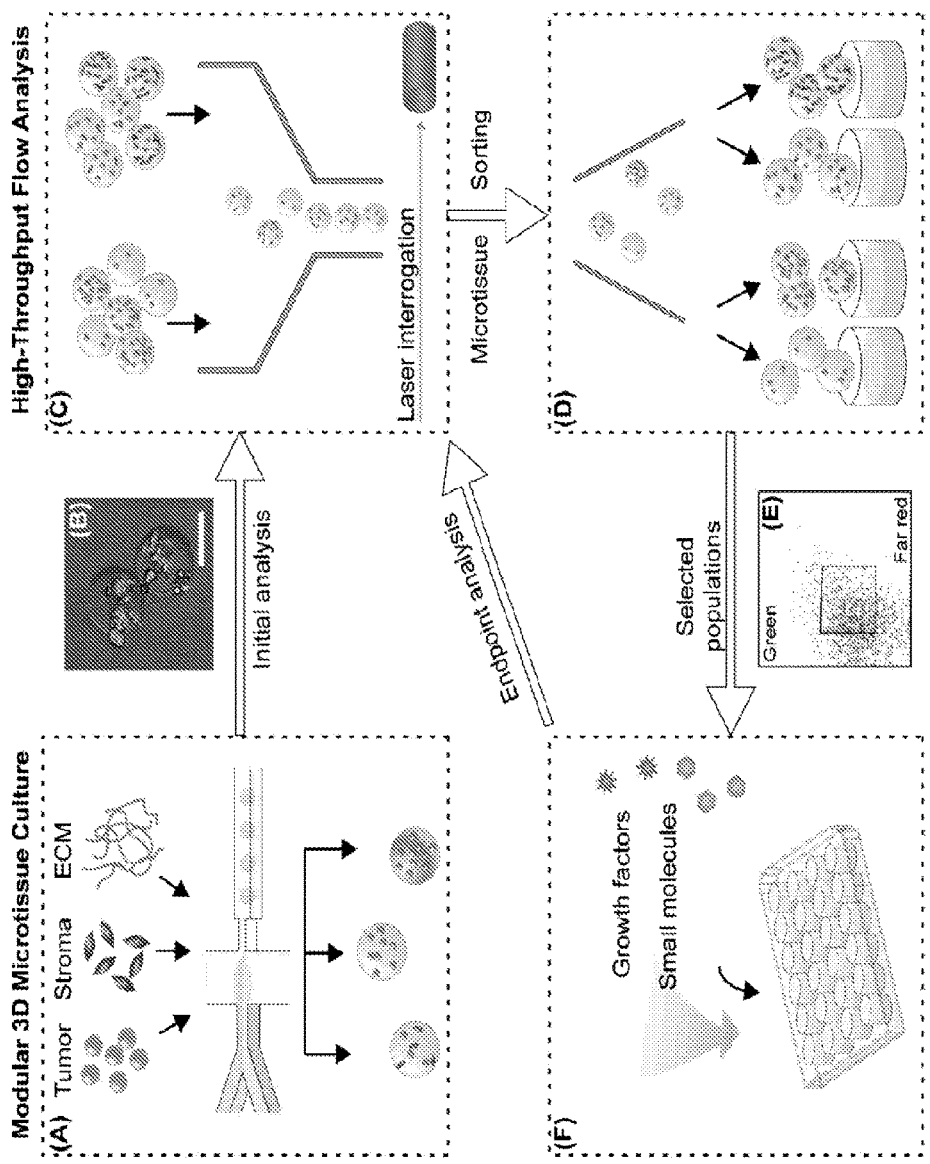
FIG. 14. Depicts a large-particle flow sort and analyzer. Depicted is a split-injection encapsulation chip with a large-particle flow analyzer and sorter (COPAS Biosort by Union Biometrica). Cells can be encapsulated within microtissues that can contain tumor cells, stromal cells, and various entrapped ECM. These microtissues can then be further enriched using the flow sorter that measures the fluorescence intensity each microtissue FIG. 15. a) Homotypic control: microtissue populations sorted into three bins (low-green, medium-pink, and high-blue) by flow-analyzer fluorescence correlate closely with average number of encapsulated cells per microtissue. b) Using fluorescence as a measure of cell density, the histogram of each microtissue population distinctly shifts right during culture as cells proliferate. (c-d) Heterotypic control: microtissues containing two cell types labeled green or far-red can be sorted into user-defined bins such as low stromal/tumor cell ratio (c) or high stromal/tumor ratio (d).

Alternatively, rather than a microfluidic device, microtissues, e.g., hepatic tissues, can be placed in a "Transwell"-like chamber where tissues are separated from fluid by a membrane. Preferably, membrane pores are of a size sufficient to capture microtissues or microgels but allow for the ready exchange of media components. Perfusion can then occur through the fluid chamber and interact with the microtissues, allowing metabolism and secreted products to be detected, for example, in the outlet of an appropriate apparatus (FIG. 13).

The methodology of the invention is generally applicable to assembly of any type of microtissue, whether by DNA or by packing in a microfluidic chamber. In exemplary aspects of the invention, the microtissues can be hepatic microtissues, as described above, or cancer microtissues (see below), etc.

It has been possible, for example, to leverage the throughput and modularity of the encapsulation devices of the invention towards an integrated in vitro 3D tumor model platform. Existing 3D culture models typically require large cell numbers and use complex endpoints (e.g. imaging or bulk biochemical assays), and many offer only limited control of the microenvironment (e.g. spatial cell density in spheroid cultures). Using a large-particle flow sort and analyzer, we have demonstrated the ability to define microtissue populations by homotypic or heterotypic cell densities, and rapidly read responses to microenvironmental cues such as ECM, growth factors, and inhibitors.

In an exemplary aspect, a in vitro 3D tumor model platform combines the split-injection encapsulation chip (described in the Examples) with a large-particle flow analyzer and sorter (COPAS Biosort by Union Biometrica). Cells can be encapsulated within microtissues (~5000/min) that can contain tumor cells, stromal cells, and various entrapped ECM. These microtissues can then be further enriched using the flow sorter that measures the fluorescence intensity each microtissue.

The following materials, methods and examples are meant to be illustrative only and are not intended to be limiting.

INTRODUCTION TO THE EXAMPLES

The three-dimensional microscale architecture of living tissues provides vital environmental cues, including extracellular matrix, soluble factors and cell-cell interactions.[1-2] Paracrine and autocrine cell signaling are critical factors guiding tissue development[3-4] and maintenance,[5-6] and dysregulation of these cues contributes to the pathogenesis of diseased states such as cancer.[7-9] Understanding and emulating these cell-cell interactions has been shown to be critical in engineering functional tissues in both 2D[10-13] and 3D[14-16] systems. In 3D culture, top-down approaches for organizing multiple cell types such as dielectrophoresis,[17-18] photopatterning,[19-20] and microfabrication[21] provide high-precision control over cell placement, but are challenging to scale-up for the assembly of mesoscale tissues.

In contrast, bottom-up methods, wherein small tissue building blocks are assembled into larger structures, have potential for constructing multicellular constructs in a facile, scalable fashion.[22-26] Living tissues are comprised of repeating units on the order of hundreds of microns; therefore, synthetic microtissues comprised of cell-laden hydrogels in this size range[27] represent appropriate fundamental building blocks of such bottom-up methods. Synthetic microtissues of this size have been previously assembled in packed-bed reactors[22, 28] or by hydrophobic/hydrophilic interactions[24, 29] but without the ability to specify the placement of many different microtissues relative to one another. One potential method for controlled assembly of heterostructures would be to incorporate the specificity of biomolecular interactions with surface templating to direct assembly. This approach could allow for scalable patterning of multiple cell types into arbitrary architectures with high precision.

In this work, we harness the well-characterized molecular recognition capabilities of DNA to achieve rapid templated assembly of multiple microtissue types (FIG. 1). This method is enabled by the high-throughput production of spherical cell-laden microtissues from a microfluidically-derived, monodispersed emulsion of a photocurable hydrogel. Cell-laden microtissues are derivatized with single-stranded oligonucleotides and integrated with custom DNA microarray templates. Orthogonal DNA sequences are used to specify the assembly of multiple cell types over large (~mm) length scales with high capture efficiency. This fusion of 'bottom-up' (templated assembly) and 'top-down' (microfluidics and robotic spotting) approaches allows for unprecedented control over mesoscale tissue microarchitecture and exemplifies the potential of integrating disparate fabrication strategies.

EXAMPLES

Patterning multiple cell types is a critical step for engineering functional tissues, but few methods provide three-dimensional positioning at the cellular length scale. Here, we present a "bottom-up" approach for fabricating multicellular tissue constructs that utilizes DNA-templated assembly of 3D cell-laden hydrogel microtissues. A flow focusing-generated emulsion of photopolymerizable prepolymer is used to produce 100 μm monodisperse microtissues at rates of 30 Hz ($10^5$/hr). Multiple cell types, including suspension and adherently cultured cells, can be encapsulated into the microtissues with high viability (~97%). We then use a DNA coding scheme to self-assemble microtissues "bottom-up" from a template that is defined using "top-down" techniques. The microtissues are derivatized with single-stranded DNA using a biotin-streptavidin linkage to the polymer network, and are assembled by sequence-specific hybridization onto spotted DNA microarrays. Using orthogonal DNA codes, we achieve multiplexed patterning of multiple microtissue types with high binding efficiency and >90% patterning specificity. Finally, we demonstrate the ability to organize multicomponent constructs composed of epithelial and mesenchymal microtissues while preserving each cell type in a 3D microenvironment. The combination of high throughput microtissue generation with scalable surface-templated assembly offers the potential to dissect mechanisms of cell-cell interaction in three dimensions in healthy and diseased states as well as provide a framework for templated assembly of larger structures for implantation.

Example 1

Materials and Methods
Device Fabrication

Microfluidic device masters were fabricated on 4 inch silicon wafers using standard photolithographic methods, with SU-8 2050 photoresist (Microchem, Mass.) spin coated at 1200 rpm to create 125 μm tall features. Masters were coated with trichloro perfluorooctyl silane (Sigma-Aldrich) for 1 hr in a vacuum dessicator prior to casting polydimethylsiloxane (PDMS, Dow Corning) devices. Cured devices with inlet holes made by a 20 G dispensing needle (McMaster-Carr) were bonded to glass slides following air plasma treatment. In order to ensure a hydrophobic surface for droplet generation, Aquapel (PPG Industries) was briefly injected into the device and flushed out with nitrogen.

Ligand Conjugation

Acrylate-PEG-RGDS (SEQ ID NO: 1) peptide was prepared as previously described.[14] To conjugate streptavidin with acrylate groups, streptavidin was dissolved in 50 mM sodium bicarbonate (pH 8.5) at 0.8 mg/ml. Amine-reactive acrylate-PEG-SVA (3.4 kDa, Laysan) was added at a 25:1 molar ratio and allowed to react with the protein at room temperature for 2 hours. Conjugated acrylate-PEG-streptavidin was purified from unconjugated PEG by washing in PBS with a 30,000 MWCO spin filter (Millipore). The acrylate-PEG-streptavidin conjugate was then reconstituted to 38 uM streptavidin in PBS, sterile filtered, and stored at −20° C.

Microtissue Polymerization

Irgacure-2959 initiator (Ciba) was dissolved at 100 mg/ml in n-vinyl pyrrolidinone accelerator (Sigma-Aldrich) to make photoinitiator working solution. The basic 2× concentrated prepolymer solution consisted of 20% w/v poly(ethylene glycol) diacrylate (PEG-DA, 20 kDa, Laysan) and 2% v/v of photoinitiator working solution. Additional prepolymer ingredients included 38 uM of acrylate-PEG-streptavidin conjugate, 10 uM acrylate-PEG-RGDS (SEQ ID NO: 1), and/or 1% v/v of fluorescent microspheres (2% solids, Invitrogen) as markers.

The final 2× prepolymer solution was injected into the microencapsulation device in parallel with, for cell-free microtissues, a 1:1 diluting stream of PBS. Syringe pumps were used to control the flow rates of the aqueous phases and the oil phase, which consisted of the perfluoro polyether, Fomblin (Y-LVAC, Solvay Solexis), with 0-2 w/v % Krytox 157 FSH surfactant (DuPont). Prepolymer droplets were gelled on-chip by exposure to 500 mW/cm$^2$ of 320-390 nm UV light (Omnicure S1000, Exfo) for an approximately one second residence time under typical flow conditions. Cell-free microtissues were collected in handling buffer (PBS with 0.1% v/v Tween-20), allowed to separate from the oil phase, and washed on a 70 μm cell strainer to remove un-polymerized solutes.

Bead Hybridization

To stain for the surface-availability of ssDNA bound on microtissues, 1 μm NeutrAvidin biotin-binding beads (yellow-green, Invitrogen) were coated with the complementary 5' biotin-DNA (IDTDNA). The original suspension of beads (1% solids) was diluted 1:10 with BlockAid blocking solution (Invitrogen), sonicated for 5 minutes, and then incubated with a final concentration of 4 μM 5' biotin-DNA for 1 hour at room temperature. Beads were then washed three times in PBS by centrifugation at 2000×g. DNA-functionalized microtissues were incubated overnight on a room-temperature shaker with coated beads resuspended to 0.1% solids in BlockAid.

Microarray Spotting

Microarray templates were printed in-house using a contact-deposition DNA spotter (Cartesian Technologies) with a 946 MP10 pin (Arrayit). Complementary pairs of single-stranded oligonucleotides used to functionalize microtissues and template their assembly are listed below and consisted of a poly-A linker followed by a heterogeneous 20 nucleotide sequence. The 20-nucleotide binding region of A and A' are complementary, B and B', etc. Sequences were modified with 5'-amine groups for microarray spotting, and 5'-biotin groups for microtissue functionalization.

| Label | Sequence | |
|---|---|---|
| A  | 5'-AAAAAAAAAAGCCGTCGGTTCAGGTCATA-3' | (SEQ ID NO: 2) |
| A' | 5'-AAAAAAAAAATATGACCTGAACCGACGGC-3' | (SEQ ID NO: 3) |
| B  | 5'-AAAAAAAAAAGACACGACACACTGGCTTA-3' | (SEQ ID NO: 4) |
| B' | 5'-AAAAAAAAAATAAGCCAGTGTGTCGTGTCT-3' | (SEQ ID NO: 5) |
| C  | 5'-AAAAAAAAAAGCCTCATTGAATCATGCCTA-3' | (SEQ ID NO: 6) |
| C' | 5'-AAAAAAAAAATAGGCATGATTCAATGAGGC-3' | (SEQ ID NO: 7) |
| D  | 5'-AAAAAAAAAATAGCGATAGTAGACGAGTGC-3' | (SEQ ID NO: 8) |
| D' | 5'-AAAAAAAAAAGCACTCGTCTACTATCGCTA-3' | (SEQ ID NO: 9) |

5'-amino oligonucleotides (IDTDNA) for templating were dissolved in 150 mM phosphate buffer (pH 8.5) at concentrations up to 250 µM, and spotted on epoxide coated slides (Corning) at 70% RH. Patterned slides were then incubated for 12 hours in a 75% RH saturated NaCl chamber, blocked for 30 minutes in 50 mM ethanolamine in 0.1M Tris with 0.1% w/v SDS (pH 9), and rinsed thoroughly with deionized water.

DNA-Directed Assembly

Microtissues containing PEG-streptavidin were incubated with 1 nmol of 5'-biotin oligonucleotides per 10 ul of packed microtissues for one hour at room temperature or overnight at 4° C. Un-bound oligonucleotides were removed by washing microtissues on a 70 µM cell strainer or using 100,000 MWCO spin filters. Multi-well chambers (ProPlate, Grace Bio-Labs) were assembled over templating slides, and DNA-functionalized microtissues were seeded in a concentrated suspension over the microarray patterns. Microtissues quickly settled into a monolayer, which was visually confirmed under a microscope. Unbound microtissues were washed off the template by gently rinsing the slide with several ml of handling buffer. Capture efficiency was quantified by measuring the average seeding density of settled microtissues in a 4× microscope field of view, divided by the average capture density over replicate spots on a slide. Percent of maximum packing fraction was calculated as the ratio of capture density to the theoretical density of close-packed circles.

Cell Culture

J2-3T3 fibroblasts were cultured in Dulbecco's Modified Eagle Medium (DMEM, Invitrogen) with 10% bovine serum (Invitrogen), 10 U/ml penicillin (Invitrogen), and 10 mg/ml streptomycin (Invitrogen). TK6 lymphoblasts (suspension culture) and A549 lung adenocarcinoma cells were cultured in RPMI 1640 with L-glutamine (Invitrogen) and 10% fetal bovine serum (Invitrogen), 10 U/ml penicillin, and 10 mg/ml streptomycin. All cells were cultured in a 5% $CO_2$ humidified incubator at 37° C.

Cell Encapsulation

Prior to encapsulation, adherent cells (J2-3T3 and A549) were detached with 0.25% trypsin-EDTA (Invitrogen). Cell pellets were resuspended at cell densities between $10\times10^6$ cells/ml and $30\times10^6$ cells/ml in an isopycnic injection medium consisting of 20% v/v OptiPrep (Sigma-Aldrich) in serum-free DMEM. Isopycnic cell suspensions were injected into microencapsulation devices in place of the diluting stream of PBS, along with 2× prepolymer solution. Gelled microtissues were collected and handled in culture media. To assess cell viability after 3 hours, microtissues stained with calcein AM (1:200, 1 mg/ml in DMSO, Invitrogen) and ethidium homodimer (1:400, 1 mg/ml in DMSO, Invitrogen) for 15 minutes at 37° C. Alternatively, microtissues for DNA-templated assembly were marked with CellTracker Green CMFDA (1:200, 5 mg/ml in DMSO, Invitrogen) or CellTracker Blue CMAC (1:200, 5 mg/ml in DMSO, Invitrogen) for 1 hour at 37° C.

Imaging and Visualization

Images were acquired with a Nikon Ellipse TE200 inverted fluorescence microscope, a CoolSnap-HQ Digital CCD Camera, and MetaMorph Image Analysis Software. NIH software ImageJ was used to uniformly adjust brightness/contrast, and pseudocolor, merge, and quantify images. Confocal images were acquired with an Olympus FV 1000 multiphoton microscope and Olympus Fluoview software. NIS-Elements software was used to pseudocolor and reconstruct maximum intensity, slice, and volume views.

Example II

High-Throughput Microtissue Fabrication

Figure 2A:
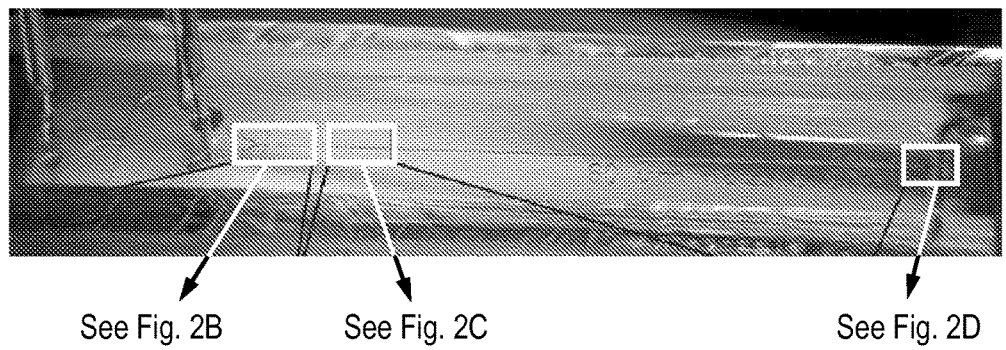
FIG. 2. Microencapsulation device. (a) Overview of device showing two aqueous input streams (red, blue) dispersed by shear flow from an oil stream into droplets that mix (purple) and travel down the UV-exposure channel. (b) Prepolymer (2× concentrated) and a cell suspension meet and flow into a 60 µm droplet generating nozzle. Vertical columns on either side of the channel provide visual references (50-100 µm below, 100-150 µm above) for real-time adjustment of droplet size. (c) Droplets pass through a bumpy serpentine mixer section to thoroughly disperse cells in prepolymer and are then polymerized by UV irradiation from a curing lamp. (d) Microtissues collected from the device (6000/min) are spherical and monodisperse. (e) Microtissue size is controlled by the relative flow rates of the combined aqueous phase ($Q_P$) and the continuous oil phase ($Q_O$), and increases with prepolymer:oil flow ratio. (f) Adding small amounts of Krytox 157 FSH fluorosurfactant into the oil decreased droplet diameter at all flow ratios, allowing higher prepolymer flow rates for a given microtissue size.
Figure 2B:
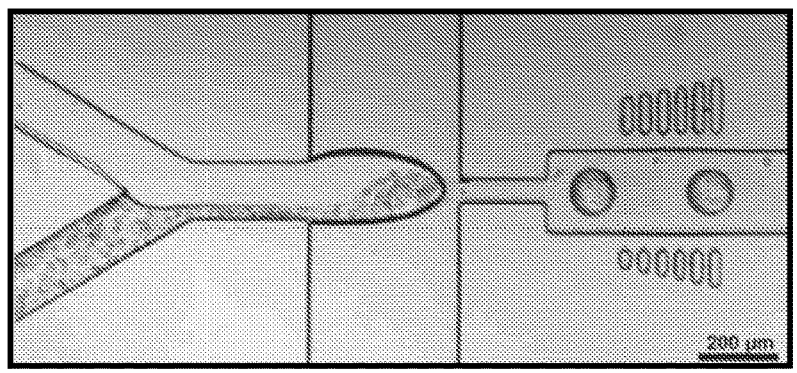
Figure 2C:
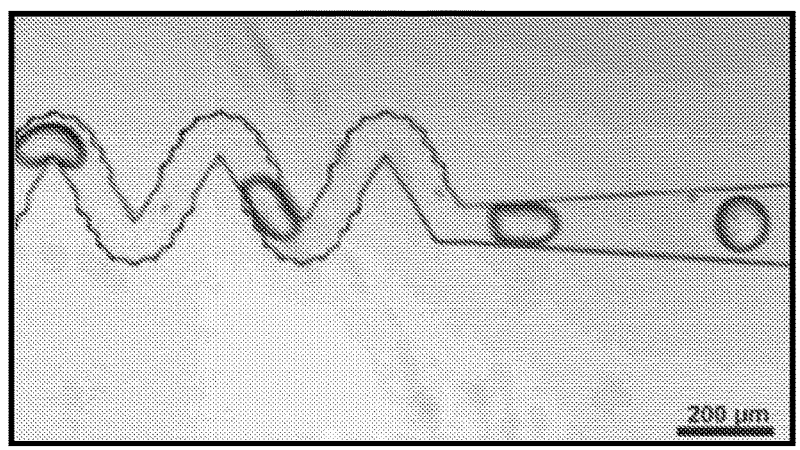
Figure 2D:
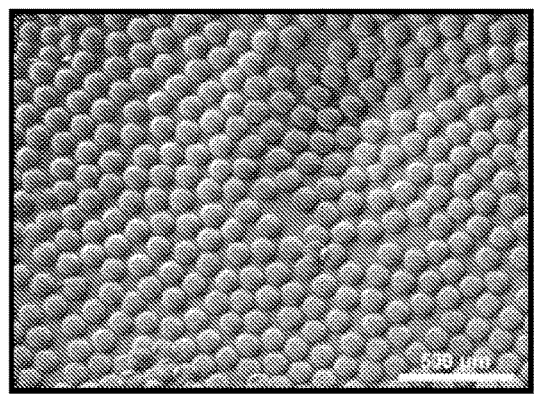
Figure 2E:
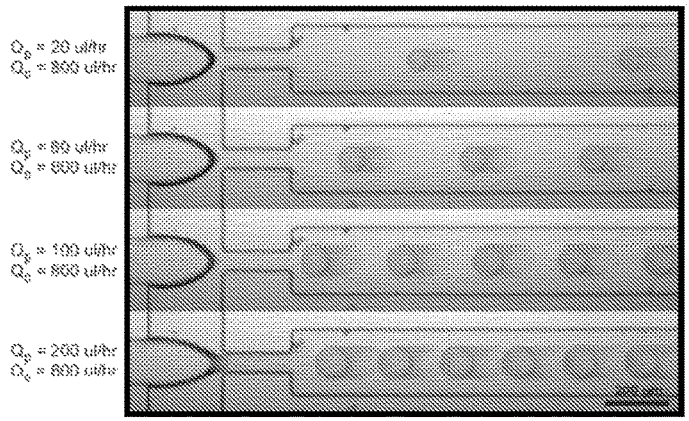
Figure 2F:
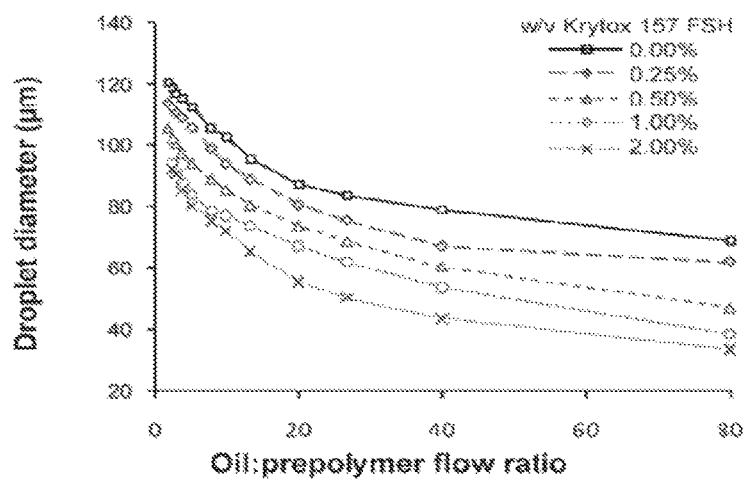

One factor restricting the application of bottom-up assembly to tissue engineering has been the low throughput of typical microtissue fabrication approaches to date, many of which are batch processes.[22, 27, 30] We first sought to design a microfluidic chip to rapidly produce uniform microtissues. Droplets generated by flow focusing of aqueous/oil phases are monodisperse and amenable to photopolymerization.[31] Thus, we fabricated a device to shear photopolymerizable poly(ethylene glycol)diacrylate (PEG) prepolymer containing cells into droplets in oil for downstream gelation by UV-light (FIG. 2a). Concentrated prepolymer was injected into the microencapsulation device as a separate stream from the cell suspension (PBS for cell-free microtissues), where the two aqueous streams were designed to meet before reaching a flow-focusing junction (FIG. 2b). With a 60 µm nozzle, shear forces were sufficient to disperse the aqueous combination into droplets that passed through a corrugated serpentine channel[32] to thoroughly mix the cell-prepolymer solution (FIG. 2c). The droplets were then polymerized by UV irradiation for 1 second during transport to the outlet. Resulting microtissues were uniformly spherical and monodisperse (FIG. 2d). We observed that by adjusting aqueous vs. oil phase flow rates (FIG. 2e) and oil-phase surfactant concentrations (FIG. 2f), we could finely control droplet diameter, and hence microtissue size, between 30-120 µm.

At a typical prepolymer flow rate of 200 ul/hr, our device was capable of achieving a production throughput of 6000 microtissues/min (~$10^5$/hr), two orders of magnitude faster than other continuous systems such as stop-flow lithography[33] (~$10^3$ particles/hr) or batch fabrication processes.[27] Microtissue fabrication by microfluidic droplet photopolymerization provides precise control over microtissue shape and size, whereas photolithographic[27] and molding[22, 24] techniques do not produce spherical gels and can suffer from resolution limits. Planar microtissue surfaces tend to adhere non-specifically to hydrophilic surfaces due to the high water content (>90%[34]) of the hydrogel material, whereas the low contact area of spherical microtissues reduces capillary adhesion during both handling and assembly. Droplet-based gels have previously been made using agarose[35] or alginate;[36] here, we chose a PEG hydrogel material for its biocompatibility and biochemical versatility. PEG-diacrylate hydrogels have high water content, are non-immunogenic and resistant to protein adsorption, and can be easily customized with degradable linkages, adhesive ligands, and other biologically or chemically active factors.[37]

Example III

Microtissue Functionalization with Surface-Encoding DNA

Figure 3A:
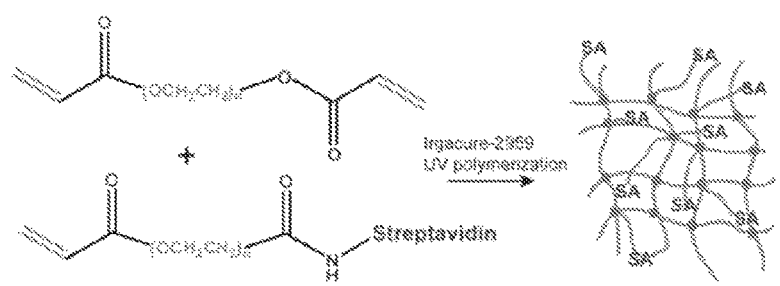
FIG. 3. Microtissue functionalization. (a) The primary hydrogel component, acrylate-PEG20k-acrylate macromonomer, was mixed with conjugated acrylate-PEG-streptavidin (0-2 mg/ml) before photo-initiated free radical polymerization, forming a hydrogel network that is decorated with pendant streptavidin proteins. (b) PEG-streptavidin microtissues stained with biotin-4-fluorescein, which can freely diffuse through the hydrogel network, and anti-streptavidin IgG which is restricted to the surface of the microtissues. The intensity of biotin-4-fluorescein staining increased linearly with the bulk concentration of covalently-bound streptavidin, while antibody stains for surface concentration increased only as a power of bulk concentration. (c) PEG-SA microtissues are further functionalized with biotin-ssDNA. The availability of this ssDNA to hybridize with a templating surface was tested using 1 µm fluorescent beads coated with DNA. (d) Microtissues with the appropriate complementary sequence were coated with hybridized beads. No beads hybridized to control-sequence microtissues, which remained dark in the green channel and showed only encapsulated marker beads in the phase image.
Figure 3B:
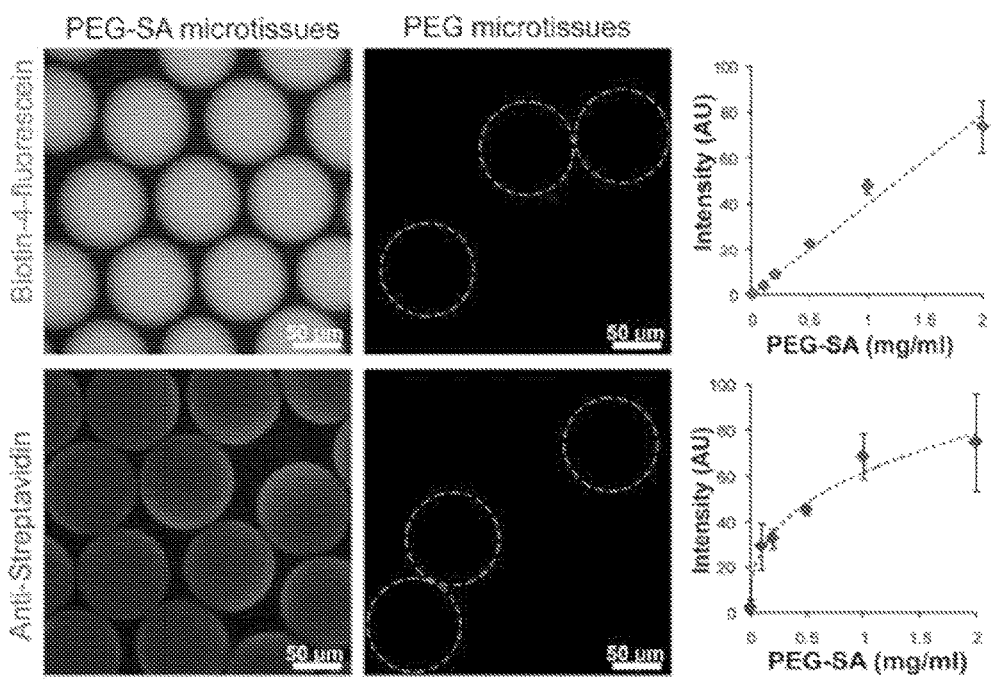

Having established a method to uniformly produce microtissues, we next sought to modify our microtissues with streptavidin for binding biotinylated DNA. To accomplish this, streptavidin was incubated with amine-reactive acrylate-PEG-SVA (3.4 kDa). Following purification, the acrylate-decorated streptavidin was then mixed into the prepolymer and covalently bound into the acrylate-PEG-acrylate hydrogel network during gelation by acrylate polymerization (FIG. 3a). Cell-free PEG-SA microtissues containing conjugated acrylate-PEG-streptavidin were stained to verify biotin-binding capacity using biotin-4-fluorescein. We also confirmed the surface-availability of streptavidin with an anti-streptavidin antibody, which was size restricted to only the surface of the microtissue (~7 nm mesh size[34]). Both biotin fluorescence and antibody staining intensities increased with the volumetric concentration of conjugated streptavidin (FIG. 3b).

Figure 3C:
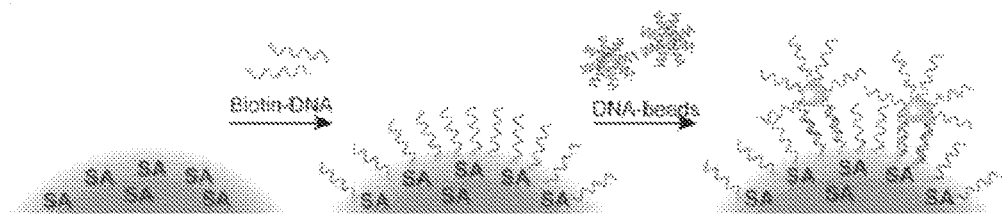
Figure 3D:
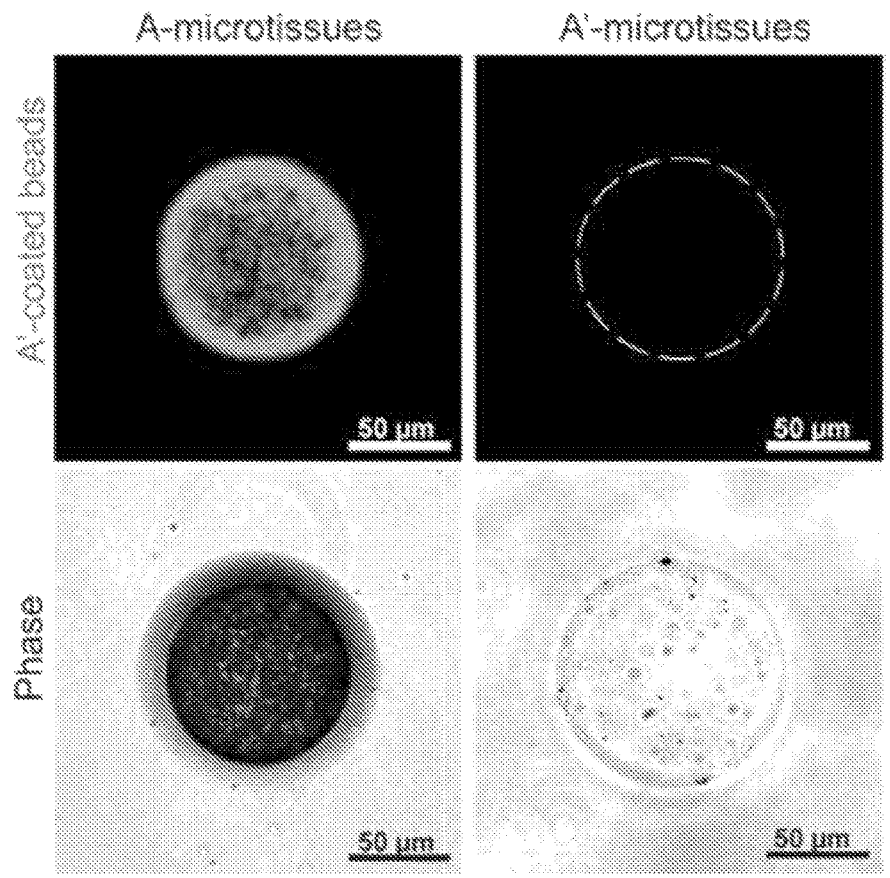

With streptavidin incorporated into the hydrogel network, we were able to encode the microtissues post-polymerization with 5'-biotin terminated oligonucleotides (FIG. 3c). Streptavidin-biotin based DNA-functionalization of microtissues is simple, modular, and cytocompatible. Post-polymerization encoding of microtissues with biotin-DNA avoids UV damage that would occur by pre-mixing acrylated-DNA into the prepolymer,[38-39] and allows the same batch of microtissues to be labeled after culture in various conditions. Other bioconjugation methods exist to modify hydrogel networks post-encapsulation, such as maleimide or NHS chemistries[40] but often require reaction conditions that are incompatible with maintaining the viability of encapsulated cells. To ensure that DNA bound to microtissues using the streptavidin-biotin interaction was available to hybridize with DNA displayed on a surface, we incubated DNA-encoded microtissues with 1 μm polystyrene beads coated with the complementary oligonucleotide (FIG. 3c). After washing to remove non-specifically bound material, microtissues encoded with the complementary sequence were thoroughly coated with beads visible as bright, punctuate spots (FIG. 3d). Conversely, beads did not specifically hybridize to control microtissues (FIG. 3d). In order to maximize bead-microtissue hybridization, we investigated conjugating acrylate-PEG-SVA to streptavidin at several molar ratios (FIG. S6). As expected, microtissues incorporating streptavidin with few acrylate pendants (10:1 molar ratio, mobility shift assay) did not promote bead hybridization as effectively as streptavidin modified with a higher number of acrylate groups (25:1 to 50:1 molar ratio), which was used for all further studies. Gels incorporating over-decorated streptavidin (1000:1 molar ratio) were also not as efficient in mediating bead-microtissue hybridization, suggesting that over-modification and/or steric hindrance plays an important role in DNA-binding capacity.

Example IV

Binding Efficiency and Specificity of DNA-Templated Assembly

Figure 4A:
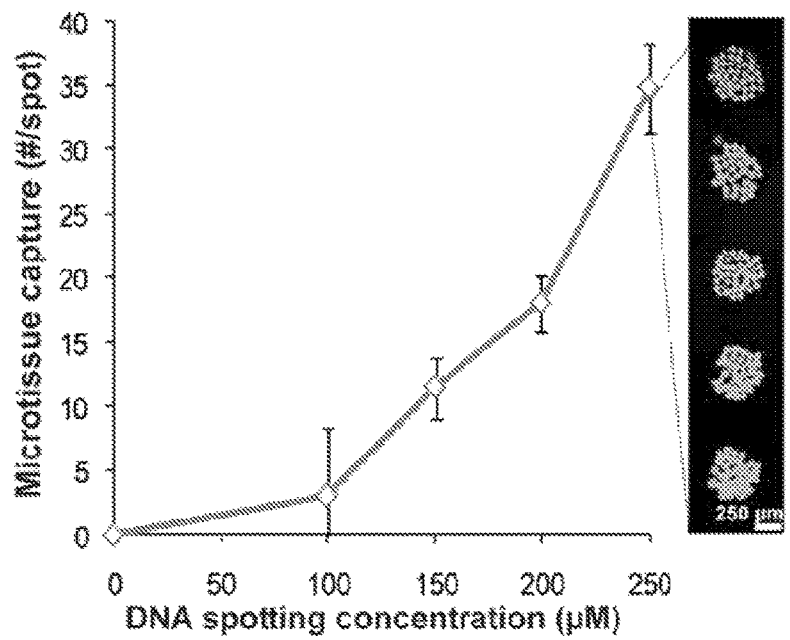
FIG. 4. Capture efficiency and specificity of DNA-directed microtissue assembly. (a) Number of DNA-functionalized microtissues containing fluorescent beads as markers captured on microarray spots with increasing spotting concentration of complementary oligonucleotide. (b) Quantified assembly results from microtissues seeded over an array of complementary spots at both high (shown on the left) and low % surface coverage. Control arrays of noncomplementary spots remained blank. Capture efficiency is calculated as the ratio of capture density to seeding density. (c) Three-color (RGB) microtissue assembly using a set of orthogonal oligonucleotide sequences: B (red), C (green), and D (blue). Microtissues contain encapsulated marker beads. (d) Quantified percentages of microtissues on target spots (1 column) vs. off-target spots (2 columns). (e) MIT logo assembled in microtissues of C (green) and D (blue), and (f) photograph of templating slide illustrating scale of assembled microtissue patterns.
Figure 4B:
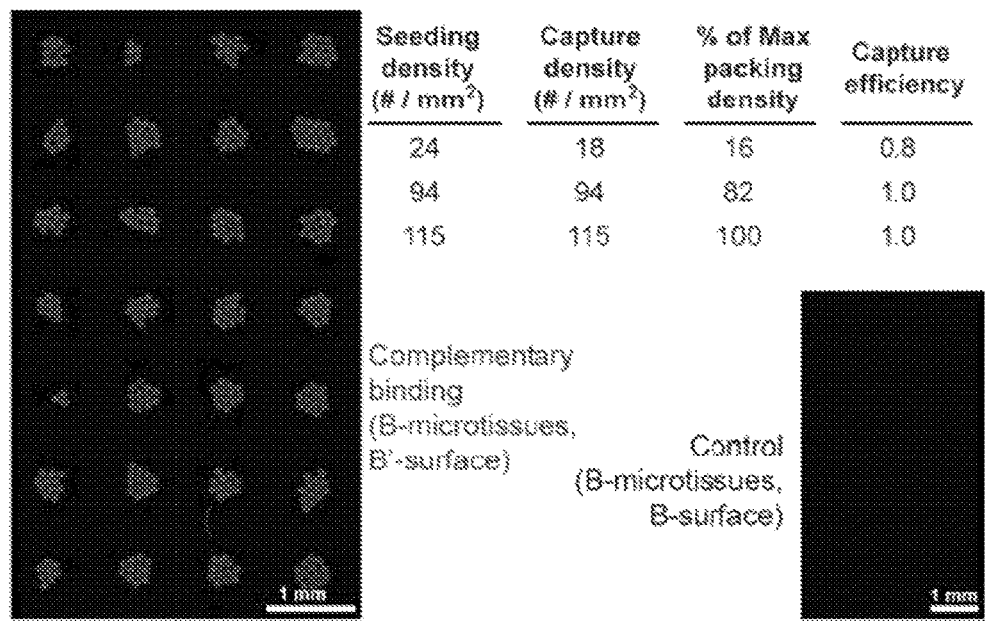

Having shown that cell-free microtissues can be coated with DNA and hybridize specifically to complementary beads, we next investigated the potential of microtissue assembly into mesoscale patterns determined by an encoded template. To create such a template, we spotted increasing concentrations of DNA (sequence A') onto a functionalized glass slide using conventional microarray technology. DNA-functionalized microtissues (A; containing green marker beads) were allowed to settle onto microarray slides from suspension, at which time non-hybridized microtissues were gently washed off the slide. The number of microtissues bound to templating array spots increased with higher spotting concentrations of templating ssDNA (FIG. 4a), plateauing at 250 μM, an order of magnitude higher than typical epoxy-silane based microarray spotting concentrations. Spots were fully covered by microtissues at this highest DNA density. To determine the capture efficiency, we seeded microtissues at varying densities (microtissues per mm$^2$, FIG. 4b). At contact-limited (hexagonally close-packed) seeding concentrations, we achieved 100% capture efficiency, indicating that if a microtissue settled onto a complementary spot, hybridization and binding would occur.

Similar efficiencies have been observed during the DNA-templated assembly of materials ranging in scale from molecules to nanoparticles to single cells[23, 41-46]. Until now, DNA-templated assembly has not been extended to larger units such as microtissues (100 μm), which present unique challenges in mass transport.[47] At these mesoscopic scales, gravity and friction become important factors in the ability of DNA-coated surfaces to sufficiently interact. During washing steps, stronger viscous drag forces on the microtissues necessitate a large number of hybridization bonds between the microtissues and templating surface to overcome microtissue removal. Here, to compensate for microtissue size, we optimize microtissue DNA functionalization and template spotting to achieve high DNA surface densities, enabling the first demonstration of large structure DNA-templated assembly.

Figure 4C:
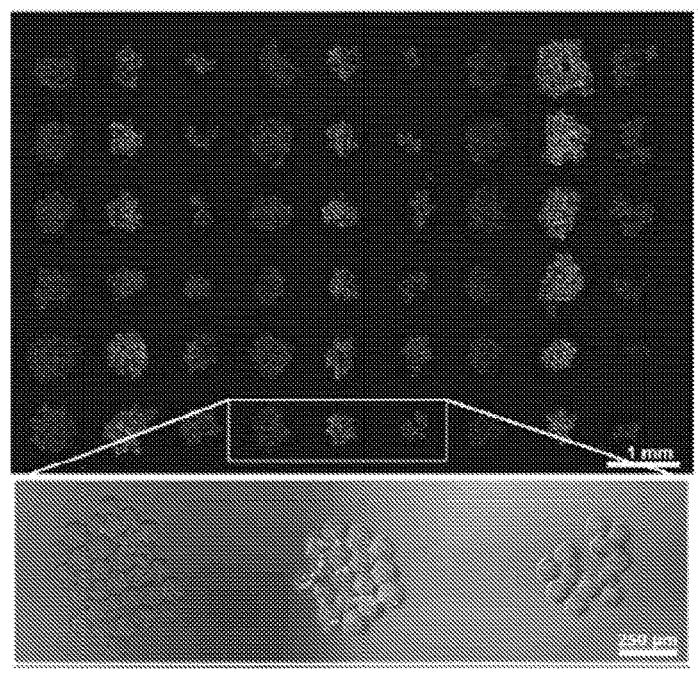
Figure 4D:
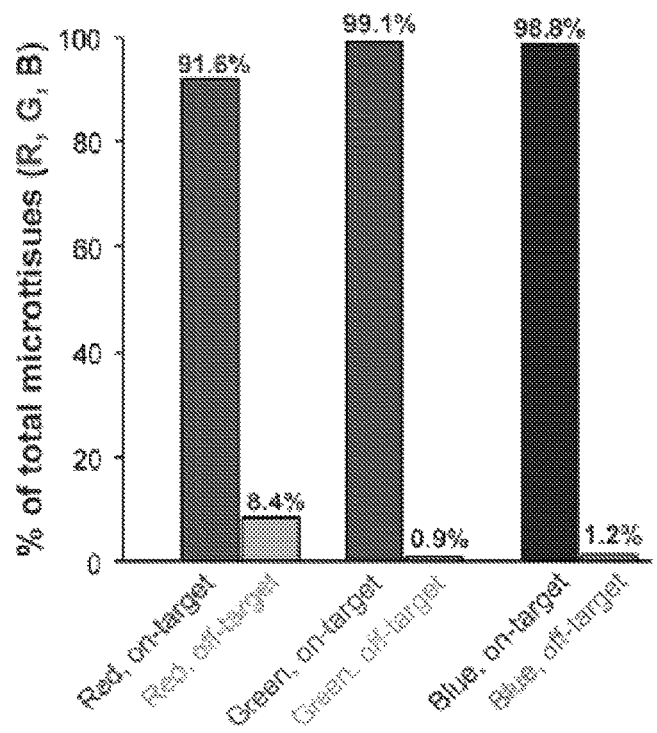
Figure 4E:
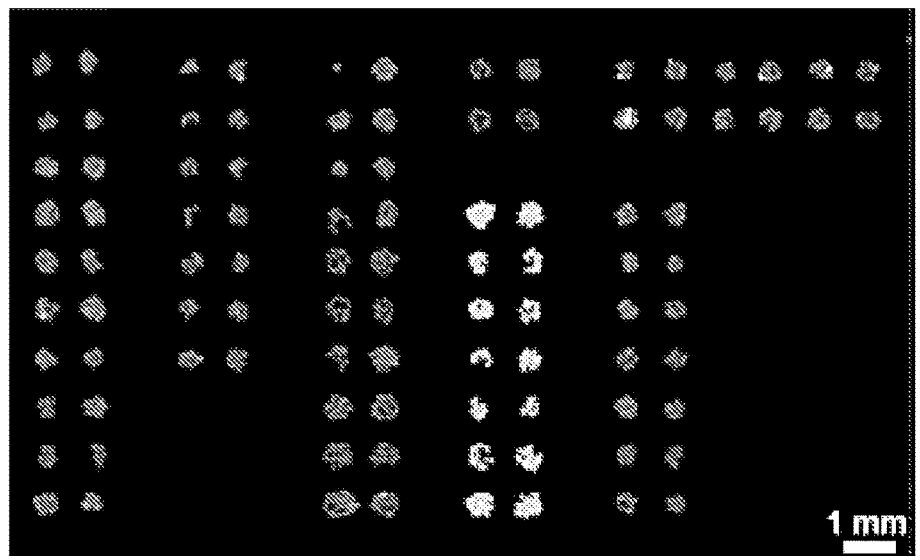
Figure 4F:
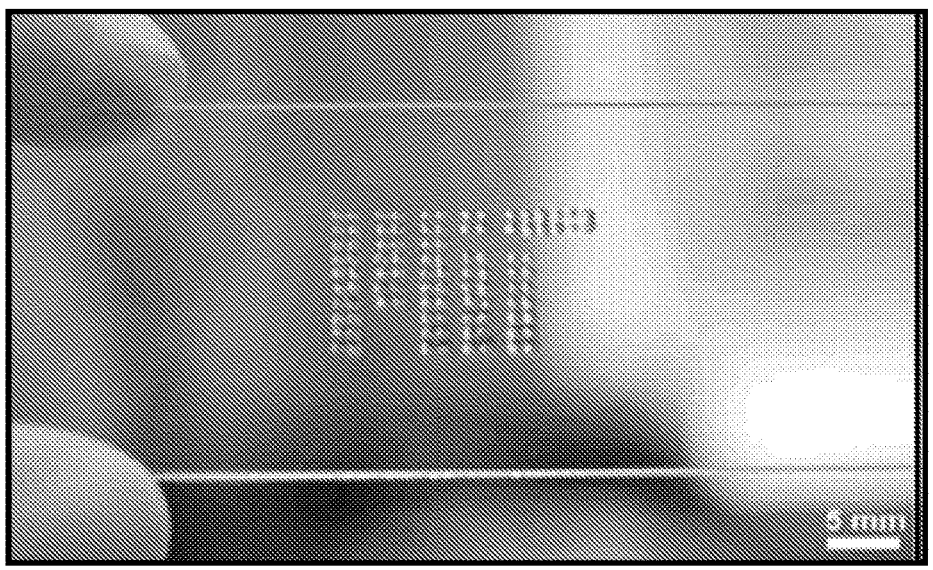
Figure 4G:
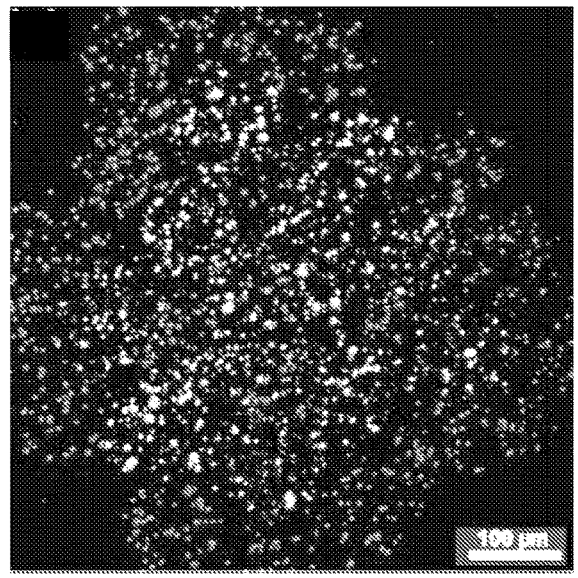
Figure 4H:
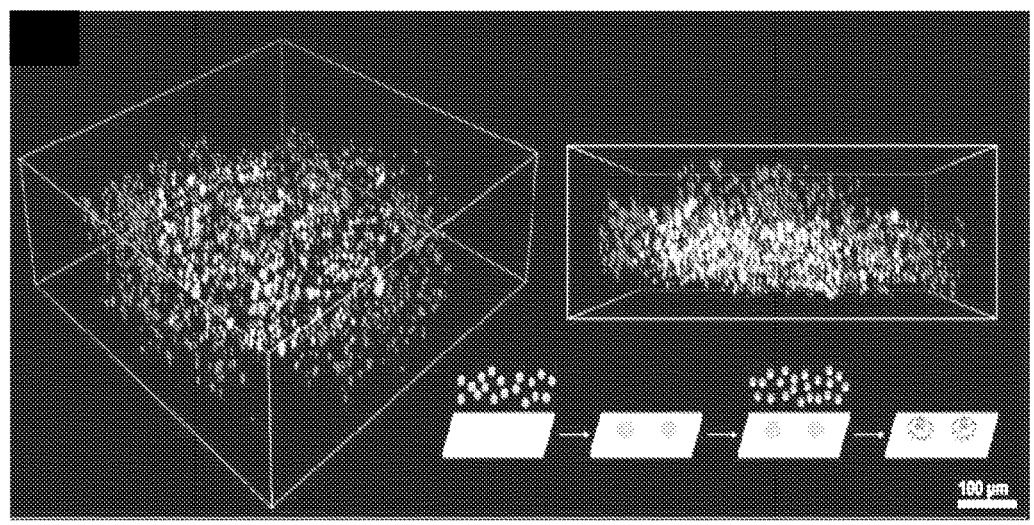

During our assembly process, minimal microtissue binding was observed between spots and on non-complementary templating spots (FIG. 4b), which was largely made possible by our control over microtissue shape. This low background binding allowed us to sequentially pattern multiple microtissue types, each encoded with an orthogonal oligonucleotide sequence, with over 90% specificity (FIG. 4c, d) and across large areas in under 15 minutes (FIG. 4e, f). Furthermore, we were able to build 3D structures (FIG. 4g, h) by filling template spots (B') with a layer of microtissues (B), and then seeding a second layer of complementary microtissues (B') that bind on and around microtissues in the first layer. Together, these experiments demonstrate the ease of achieving organizational control at macroscopic length scales by microtissue assembly.

Example V

DNA-Templated Assembly of Multicellular Tissue Constructs

Figure 5A:
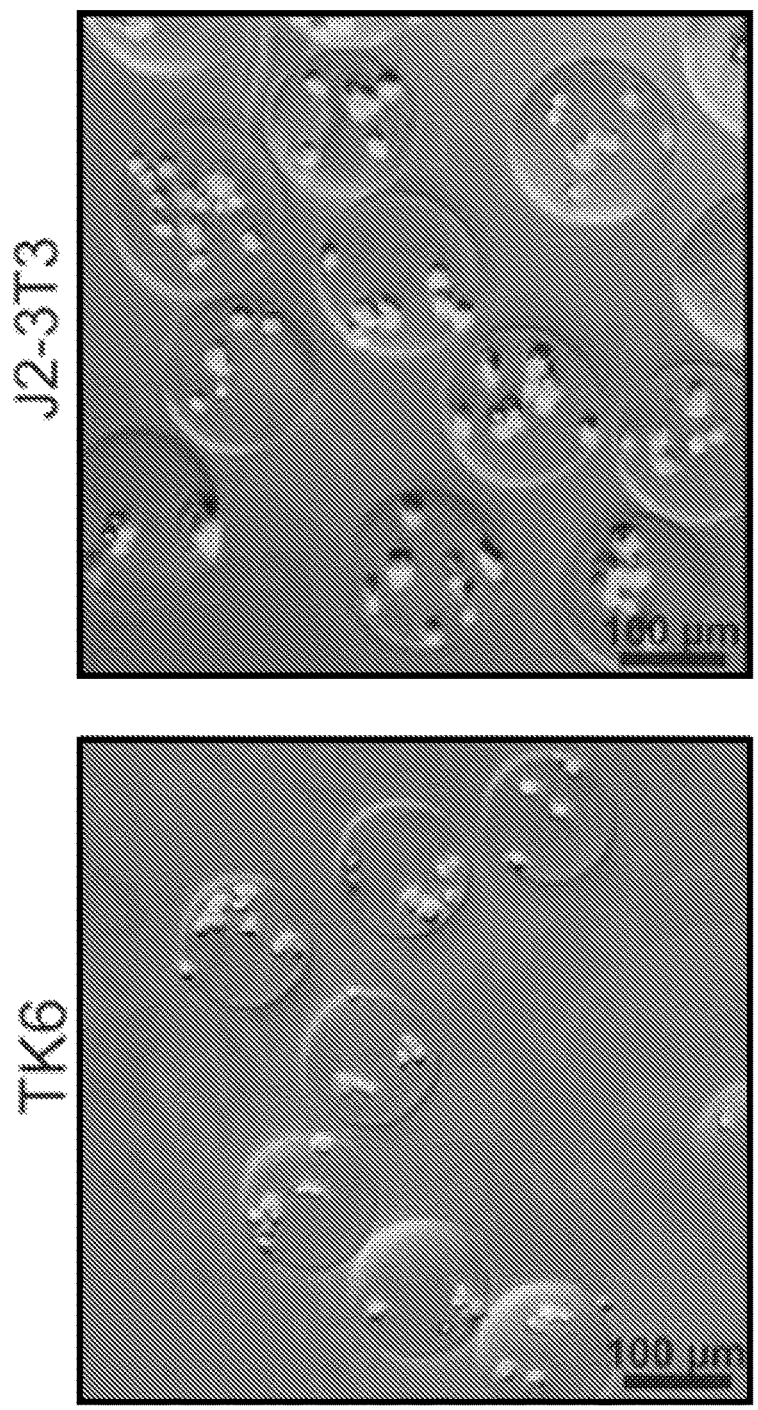
FIG. 5. Cell encapsulation and microtissue culture. (a) Rat fibroblast (J2-3T3) and human lymphoblast (TK6) cell lines uniformly encapsulated within microtissues and stained for viability. (b) Histogram of J2-3T3 5 distribution within microtissues and comparison to optimal Poisson statistics. (c) Viability of J2-3T3 and TK6 cells three hours postencapsulation at increasing % UV overexposure past the minimum intensity required to fully polymerize microtissues. (d) J2-3T3 cells attached and spread within microtissues decorated with RGDS (SEQ ID NO: 1) peptides. (e) Human lung adenocarcinoma (A549) cells aggregated to form multicellular tumor spheroids within microtissues. (f) Microtissues encapsulating either J2-3T3 (CellTracker Green) or A549 cells (CellTracker Blue) were self-assembled into composite hexagonal clusters.
Figure 5B:
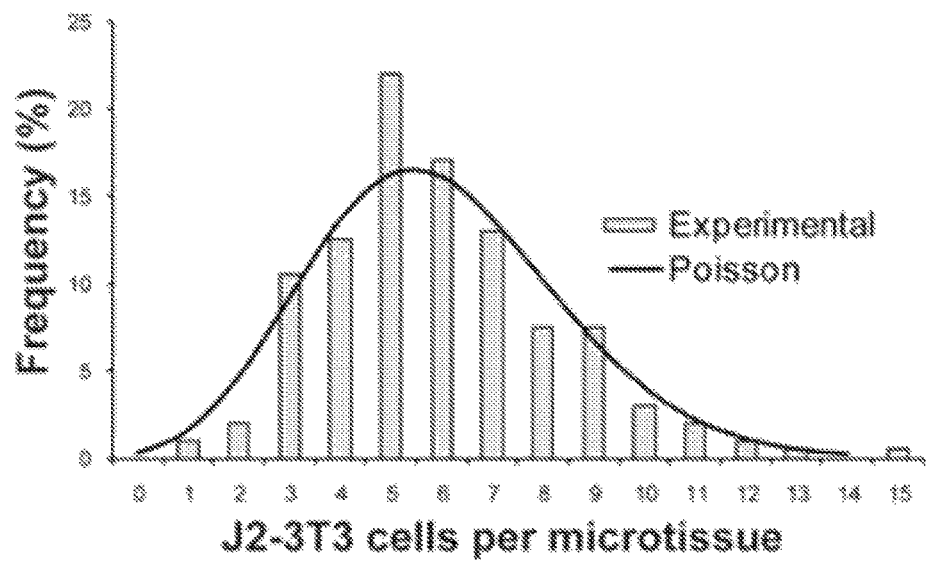
Figure 5C:
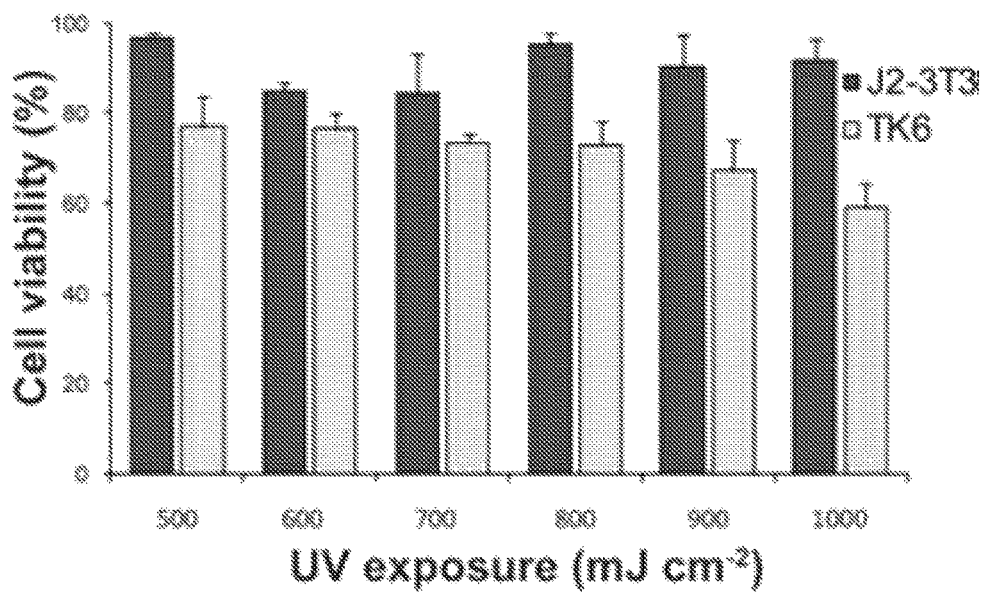
Figure 7A:
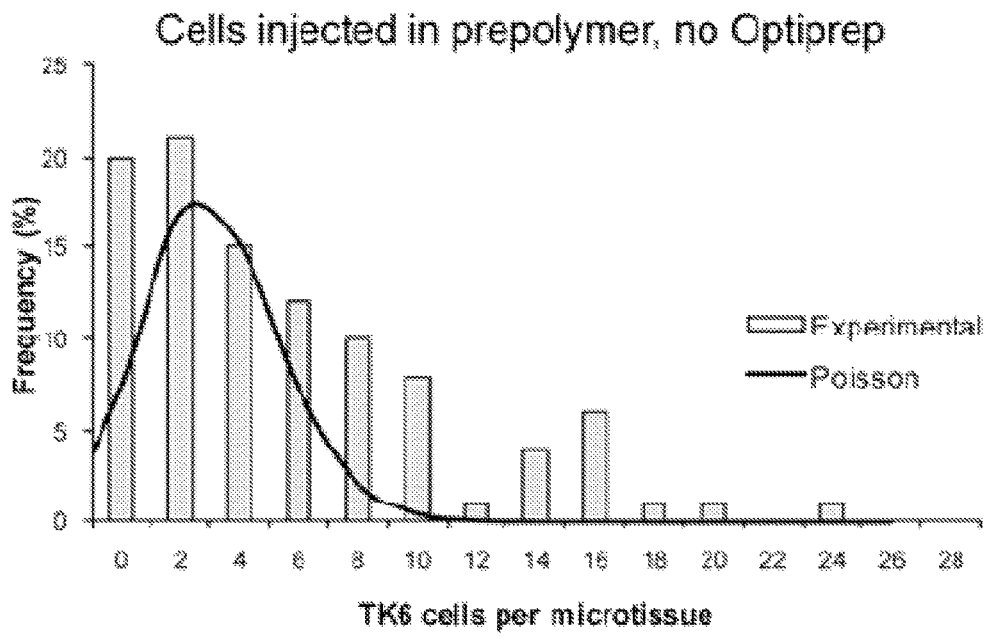
FIG. 7. Distribution of cell encapsulation numbers within microtissues. (a) Prior to process modifications, cells that were suspended in prepolymer settled within tubing between the syringe and the device, resulting in oscillating cell density reaching the nozzle and an uneven number of cells per microtissue. (b) When cells are injected in an isopycnic medium, and as a separate stream from concentrated prepolymer, the distribution narrowed to the Poisson limit.
Figure 7B:
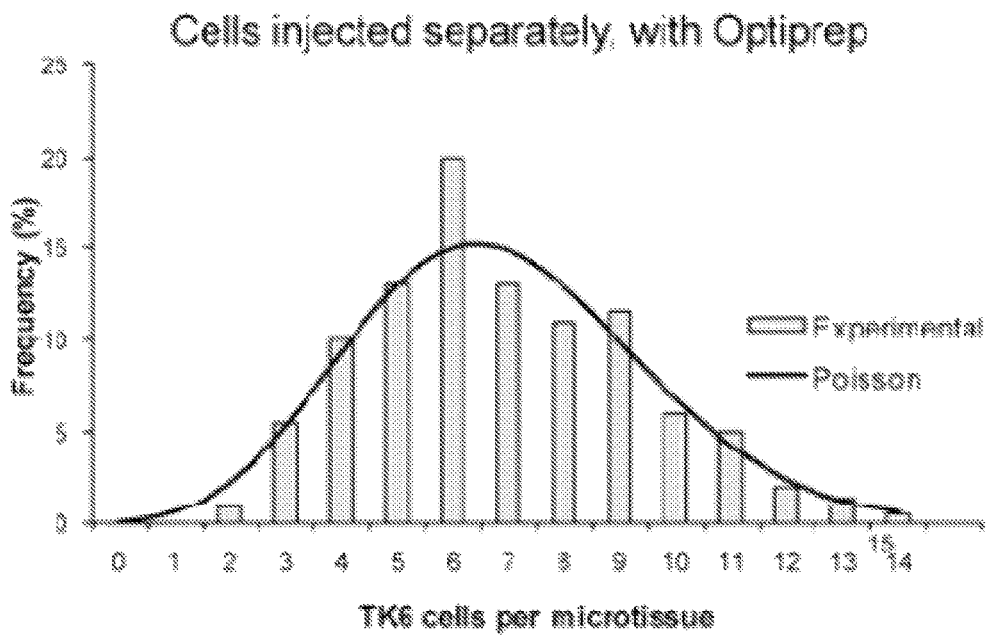
Figure 8A:
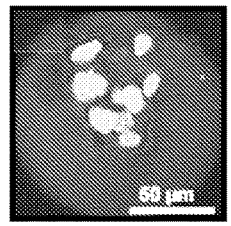
FIG. 8. Multi-photon images of fibroblast spreading within RGDS microtissues. (a) Maximum intensity projection and (b) slice images of J2-3T3 fibroblasts spreading on Day 4 post-encapsulation. Red: actin (phalloidin), green: hydrogel (biotin-4-fluorescein), bright-green: nuclei (Hoecht).

In order to apply DNA-templated patterning to the assembly of multicellular constructs, we next focused on encapsulating cells into uniform and highly viable cell-laden microtissues. To improve the consistency of cell encapsulation (FIG. 7), we increased the specific gravity of our cell suspensions to prevent cell settling during injection. We chose a density gradient medium (OptiPrep), based on an iodinated small molecule, that increases specific gravity without affecting viscosity or cross-linked hydrogel network density, and easily diffuses out of the polymerized microtissues. With these changes, we attained cell encapsulation matching a Poisson distribution (FIG. 5b). In addition, we replaced the hydrocarbon oil phase with an oxygen-permeable fluorocarbon oil (Fomblin) to allow immediate quenching of excess free radicals post-UV exposure.[48] Notably, using fluorocarbon oil, cells were able to tolerate a wide range of total UV exposures (mJ/cm$^2$) while maintaining >90% viability (FIG. 5c). As a result of these changes, several adhesive and suspension cell lines, including adherent mesenchymal (fibroblasts), nonadherent mesenchymal (lymphoblasts) and adherent epithelial (adenocarcinoma), were uniformly encapsulated into microtissues with consistently high viability (FIG. 5a). Variations in average viability between cell types (e.g. J2-3T3 vs. TK6) could be due a number of cell type differences including susceptibility to DNA damage.[49] For cell lines sensitive to UV, photoinitiators in the visible-light range could be substituted into our material system.[50]

Figure 5D:
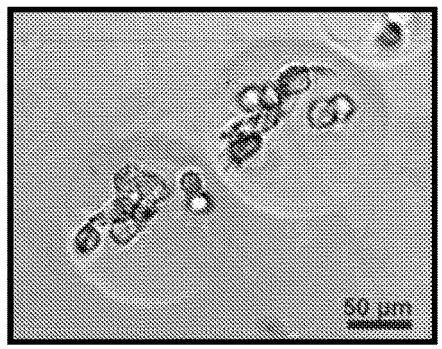
Figure 5E:
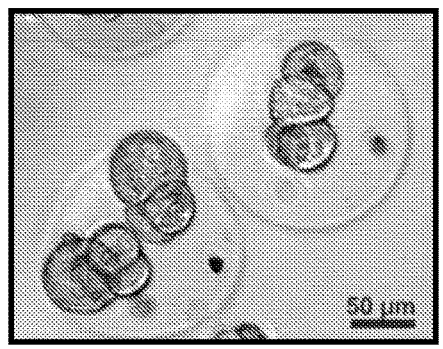
Figure 9:
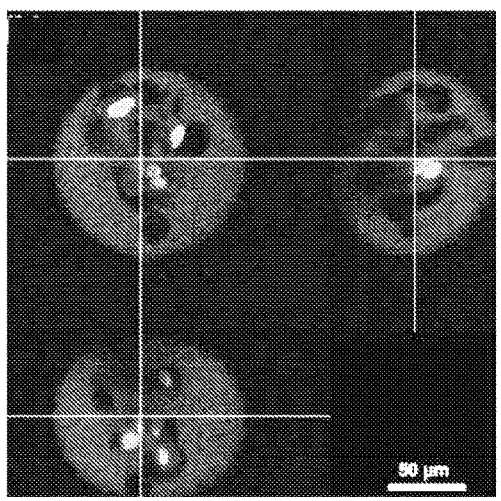
FIG. 9. Fibroblast-laden, RGD-decorated microtissues cultured in close contact and in the presence of non-encapsulated fibroblasts. Contiguous microtissue-assembled structures linked by adherent cells formed by D1 post-encapsulation.
Figure 9:
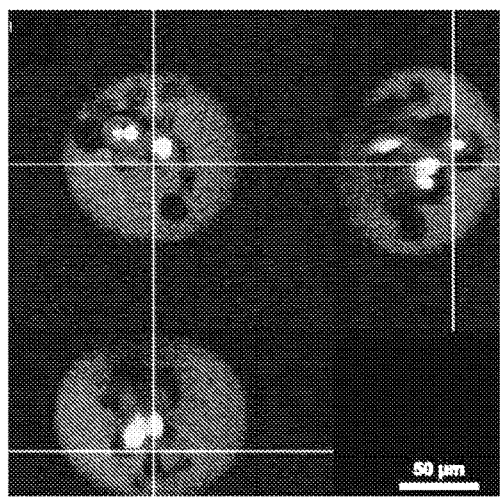
Figure 9:
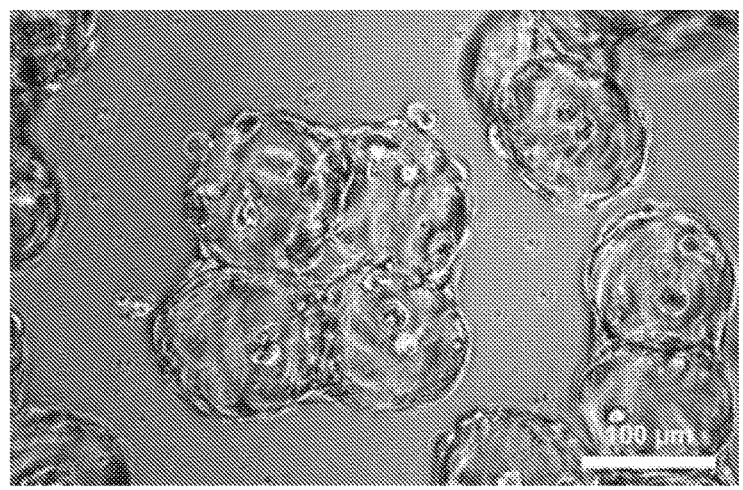

These are many advantages associated with patterning cellular microtissues rather than single cells.[43-44] Firstly, cells can be encapsulated in a modular scaffold with customized ECM molecules (e.g. RGDS)(SEQ ID NO: 1) to promote certain phenotypes. As an example, we added acrylated RGDS (SEQ ID NO: 1) peptide to the prepolymer during fibroblast encapsulation. By Day 2 post-encapsulation, fibroblasts began spreading within these adhesive microtissues (FIG. 5d). Secondly, microtissues containing one cell type can be first cultured separately to stabilize homotypic interactions before they are self-assembled with other microtissues to activate heterotypic interactions. For instance, when cultured for several days, adenocarcinoma cells encapsulated from a single-cell suspension formed multicellular spheroids (FIG. 5e). In addition, encoding DNA is bound to the hydrogel scaffold rather than directly onto the cell membrane,[43-44] where covalently bound ligands may be susceptible to recycling or may potentially modify cell function. Encoded microtissues can remain in assembled patterns for an extended period of time without additional measures for immobilization (e.g. embedding in agarose[23]), and then removed for further culture, isolation, and biochemical analysis.[27] DNA also provides a way for programmed detachment via dehybridization (e.g. competitive binding with free ssDNA) or cleavage (e.g. restriction enzymes).[43] Alternatively, patterned microtissues could be stabilized into a contiguous tissue by a secondary hydrogel polymerization[29] or cell adhesion between microtissues to form 3D sheets for implantation (FIG. 9).

Figure 5F:
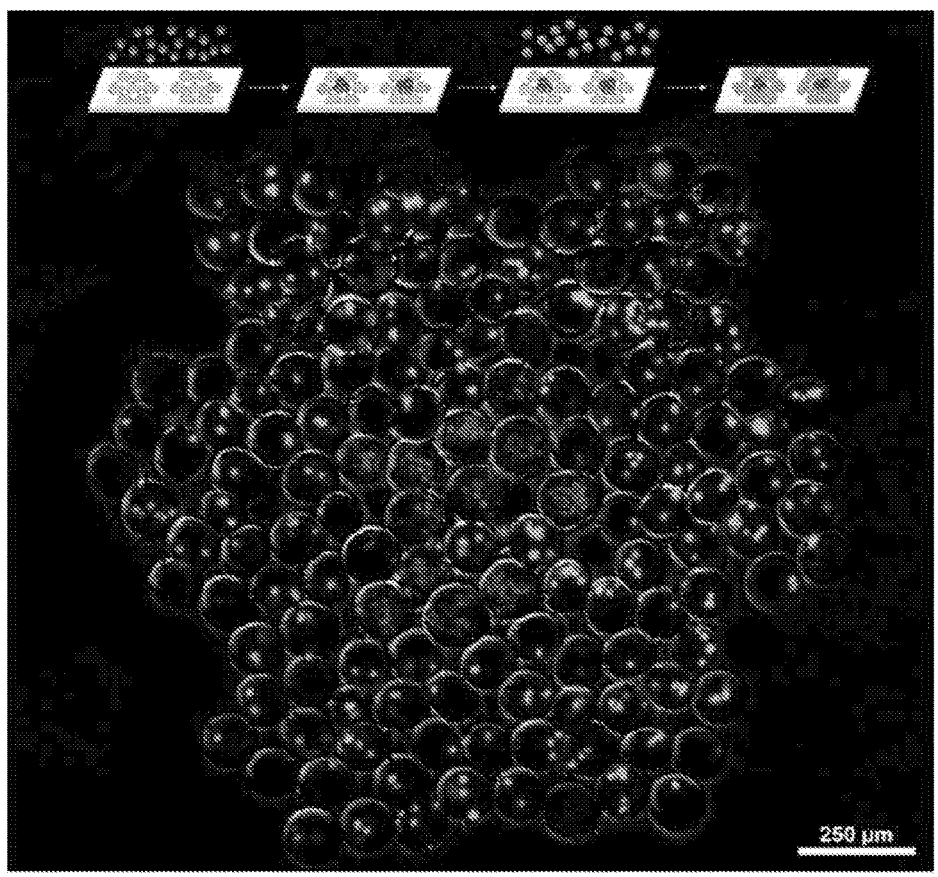
Figure 6:
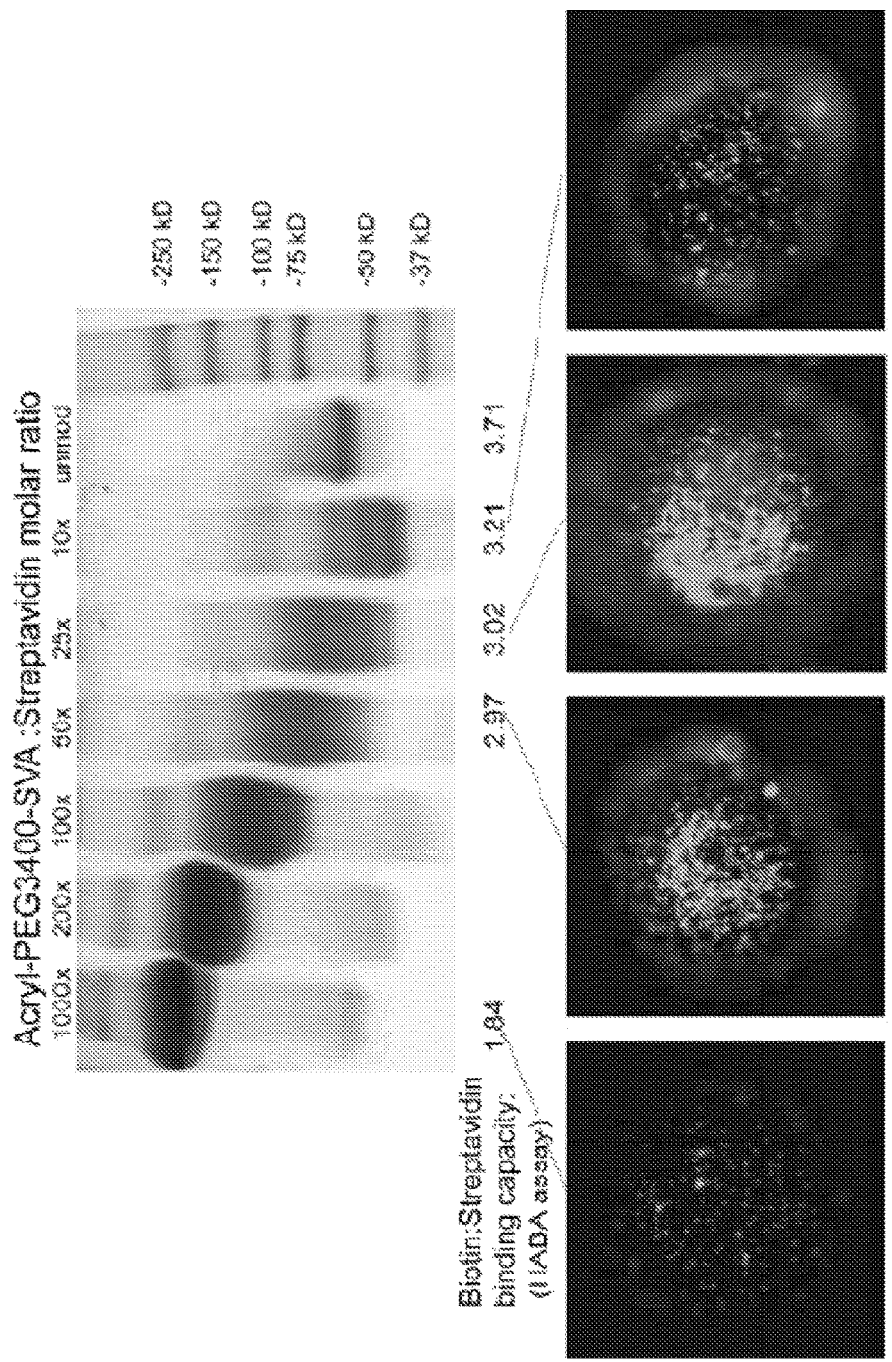
FIG. 6. Optimization of acrylate-PEG-streptavidin conjugation. Non-denaturing PAGE gel (top) of purified products from varying molar ratios of reactants. At low ratios, discrete bands of protein with 1-5 modified amines are visible. At higher ratios, streptavidin is over-modified and biotin-binding capacity is significantly reduced. Reaction conditions of interest were further tested by incorporating products into microtissues, binding biotin-DNA, and staining by hybridization with DNA-coated beads (bottom).

Finally, to demonstrate DNA-templated positioning of microtissues containing distinct cell types into pre-defined patterns, we encapsulated adenocarcinoma cells (blue) and fibroblasts (green) into separate microtissues and encoded them with orthogonal DNA sequences (C and D respectively). These microtissues were then seeded onto an array printed with hexagonal clusters of complementary DNA (C' centered within 6 spots of D'), forming co-cultures of the two cell types representative of a tumor nodule surrounded by stromal cells (FIG. 5f). Multicellular constructs patterned using this method could be relevant model systems for studying cancer-stroma interactions in 3D. Notably, although DNA-templated microtissues are patterned on a 2D template, cells are encapsulated and respond to a locally 3D microenvironment, e.g. developing into tumor spheroids (FIG. 5e) rather than growing as a 2D monolayer.[16] Heterotypic signaling from stromal cells has been shown to contribute to tumor invasion and metastasis.[9] The combination of precise spatial control, similar to that achieved in 2D,[10] but with a 3D environment, will be critical toward elucidating such cell signaling mechanisms.

Examples I-V present a method to organize multiple cell types within a 3D microenvironment that integrates the top-down patterning of a DNA microarray template with the bottom-up assembly of DNA-encoded, cell-laden microtissues. This is the first demonstration of microtissue assembly that is directed by specific biomolecular interactions. The speed and scalability of the assembly process is compatible with DNA templates that can be fabricated by other top-down techniques, such as microfabrication and micro-contact printing, for a diverse range of features and patterning resolution. The programmable molecular interaction of DNA to direct assembly has the potential to be extended to even larger sets of encoding sequences to create more complex heterogeneous structures. The ability to precisely control cell-cell interactions (e.g. cancer-stromal cell, hepatic-nonparenchymal cell) via microfluidic cell encapsulation and DNA-templated microtissue assembly provides a unique opportunity to increase our fundamental understanding of complex diseases or to construct highly functional tissue-engineered implants.

Example VI

Figure 10A:
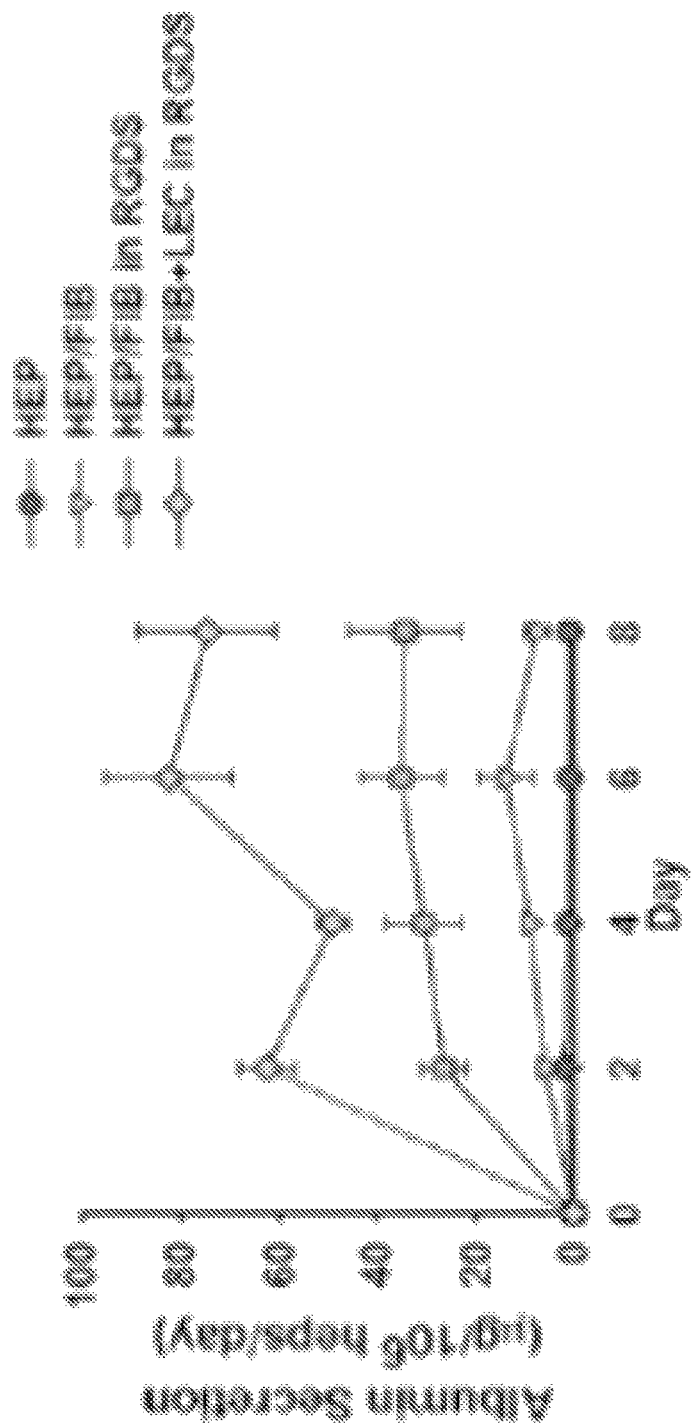
FIG. 10. A) Albumin secretion as a measure of hepatic phenotype, elevated in the presence of fibroblasts and RGDS peptide. B) Luminex bead measurements of human drug metabolism enzyme genes, showing upregulation of the genes in 3D as opposed to 2D, in various phases of drug metabolism. C) Demonstrated CYP450 activity in 3D engineered hepatic tissues, including drug-drug interactions.

This Example demonstrates that it is possible to maintain the human hepatic phenotype in 3D engineered liver tissues and demonstrated robust hepatic functions over weeks of culture, including protein synthesis, human drug metabolism, drug-drug interaction, and drug-induced liver injury (FIG. 10). Interactions with fibroblast and endothelial non-parenchymal cells were critical for the maintenance of hepatic viability and function in 3D culture; the ligation of α5β1 integrin via RGDS further improved hepatic functions (FIG. 10A). More recently, it has been possible to extend the function of 3D engineered liver tissues even further, by addition of a micropatterning step pre-encapsulation (FIG. 11).

Figure 10B:
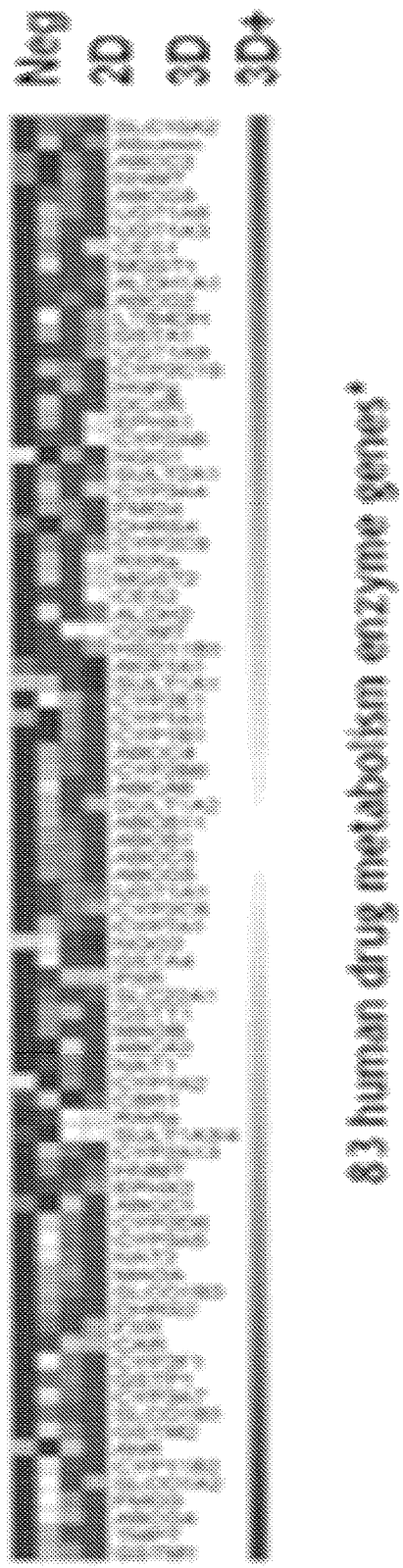
Figure 10C:
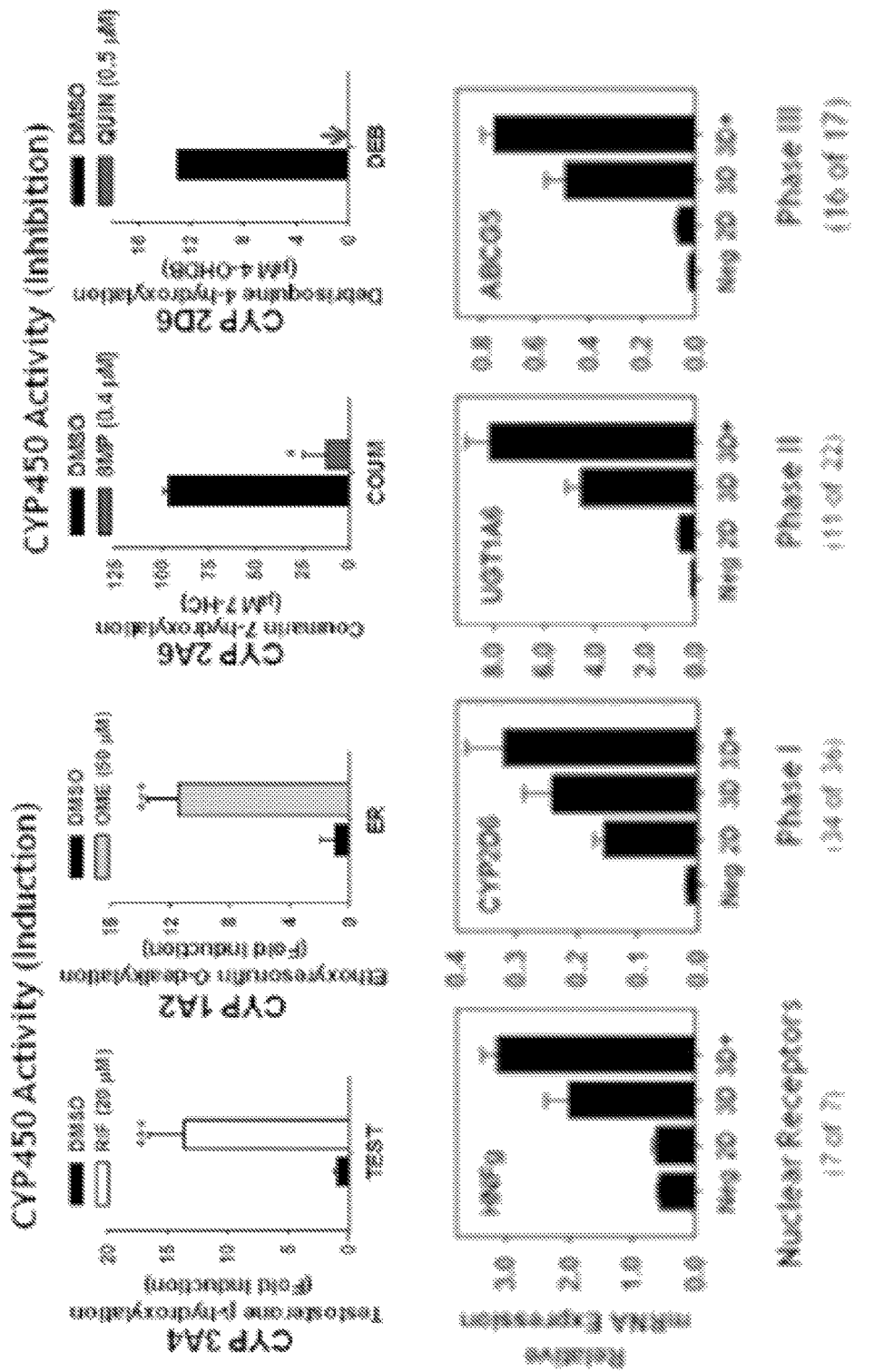
Figure 11:
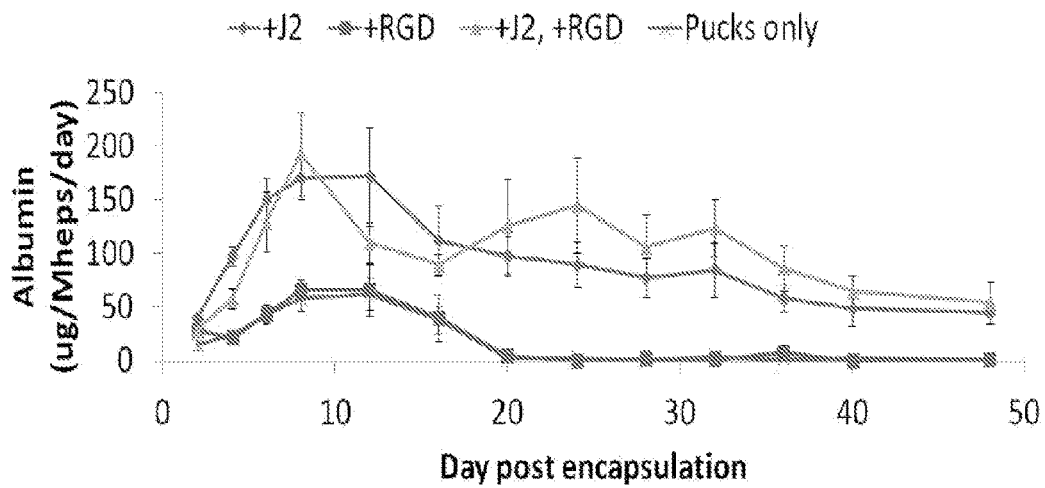
FIG. 11. Extended albumin production in the presence of J2's by pre-patterning primary hepatocytes into clusters with cell-cell contacts prior to encapsulation.

Characterization of hepatic tissues for the expression and function of human drug-metabolizing enzymes (FIG. 10B) by a high-throughput Luminex bead PCR assay demonstrated that the majority (68 of 82) of human drug metabolism-encoding transcripts were expressed in 3D hepatic tissues (FIG. 10B). Functional validation of gene expression by treatment with compounds known to induce or inhibit CYP450 enzymes showed that engineered tissues accurately predict clinical drug metabolism and interactions (FIG. 10C).

Example VII

Figure 12A:
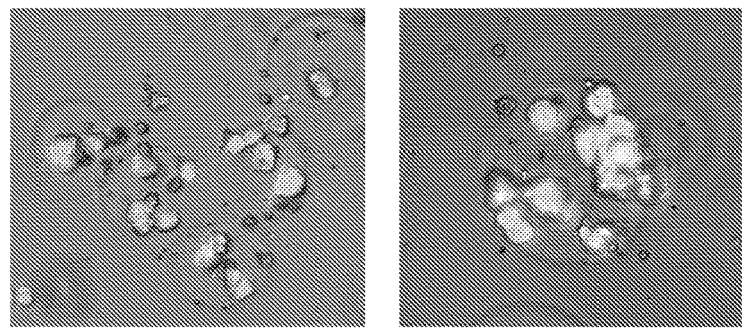
FIG. 12. Hepatic microtissues (~150 um diameter) generated by droplet-based encapsulation device, living hepatocytes stained in green. b) Hepatic microtissues respond to hepatotoxic compounds such as acetaminophen (increased red-dead signal).
Figure 12B:
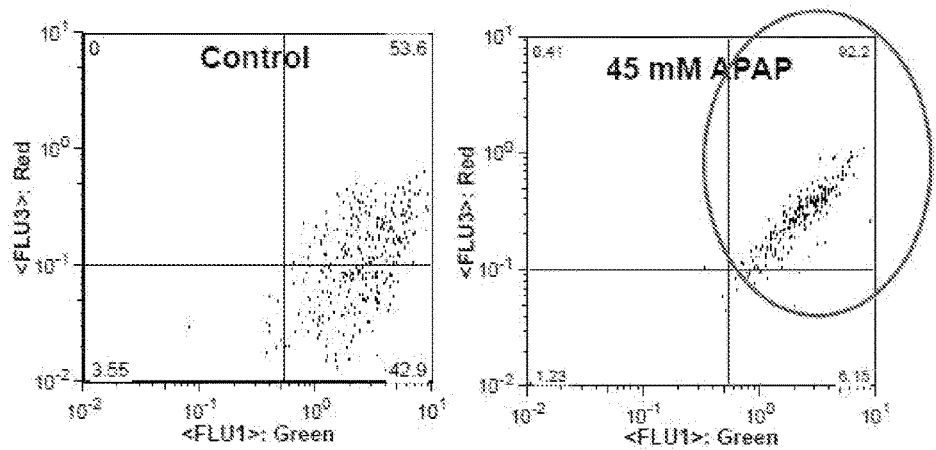

This Example demonstrates the generation of a 3D microtissue-based liver on a chip (e.g. for metabolism, drug response or disease modeling). Primary hepatocytes are encapsulated in 3D within PEG material, along with co-encapsulated cell types and/or signals needed to stabilize their function. Miniaturized versions of these 3D gels (FIG. 11) are packed into a microfluidic chamber (similar to a packed bed reactor) and media is perfused through the interstitial spaces between the gels. Alternatively, rather than a microfluidic device, hepatic tissues is placed in a "Transwell"-like chamber where tissues are separated from fluid by a membrane. Perfusion then occurs through the fluid chamber and interacts with the microtissues, allowing metabolism and secreted products to be detected in the outlet (FIG. 12).

Example VIII

This Example demonstrates that it is possible to leverage the throughput and modularity of encapsulation device of the invention towards an integrated in vitro 3D tumor model platform. Existing 3D culture models typically require large cell numbers and use complex endpoints (e.g. imaging or bulk biochemical assays), and many offer only limited control of the microenvironment (e.g. spatial cell density in spheroid cultures). Using a large-particle flow sort and analyzer, we have demonstrated the ability to define microtissue populations by homotypic or heterotypic cell densities, and rapidly read responses to microenvironmental cues such as ECM, growth factors, and inhibitors.

The in vitro 3D tumor model platform combines the split-injection encapsulation chip described in detail above with a large-particle flow analyzer and sorter (COPAS Biosort by Union Biometrica). Cells are first encapsulated within microtissues (~5000/min) that can contain tumor cells, stromal cells, and various entrapped ECM. These microtissues are then further enriched using the flow sorter that measures the fluorescence intensity each microtissue, correlating with the density of zs-green tumor cells in each microtissue. (FIG. 15a), and can sort the microtissues (~25 selected/min) into low, medium, and high homotypic cell density bins (FIG. 15b). Microtissues containing a second labeled cell type (e.g. fibroblasts labeled DDAO-far red) can also be sorted by heterotypic density and/or ratio (FIG. 15c). Selected populations of microtissues are then exposed to stimuli in culture such as growth factors and inhibitors, and their proliferation over days is detected on a population level (FIG. 15b).

Figure 16A:
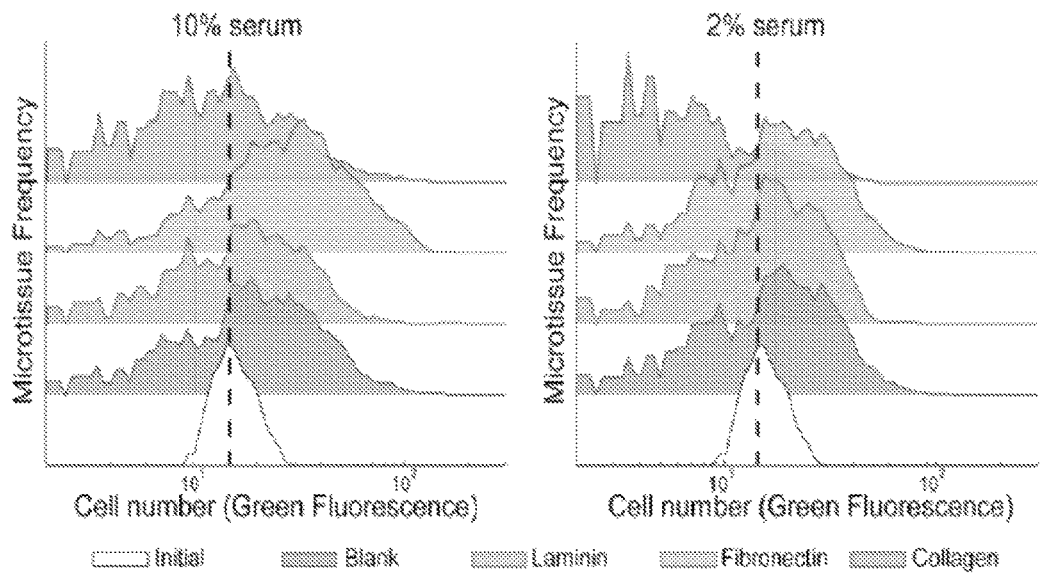
FIG. 16. Microtissue proliferation modulated by (a) incorporated extracellular matrix molecules, or (b) culture in soluble growth factors.
Figure 16B:
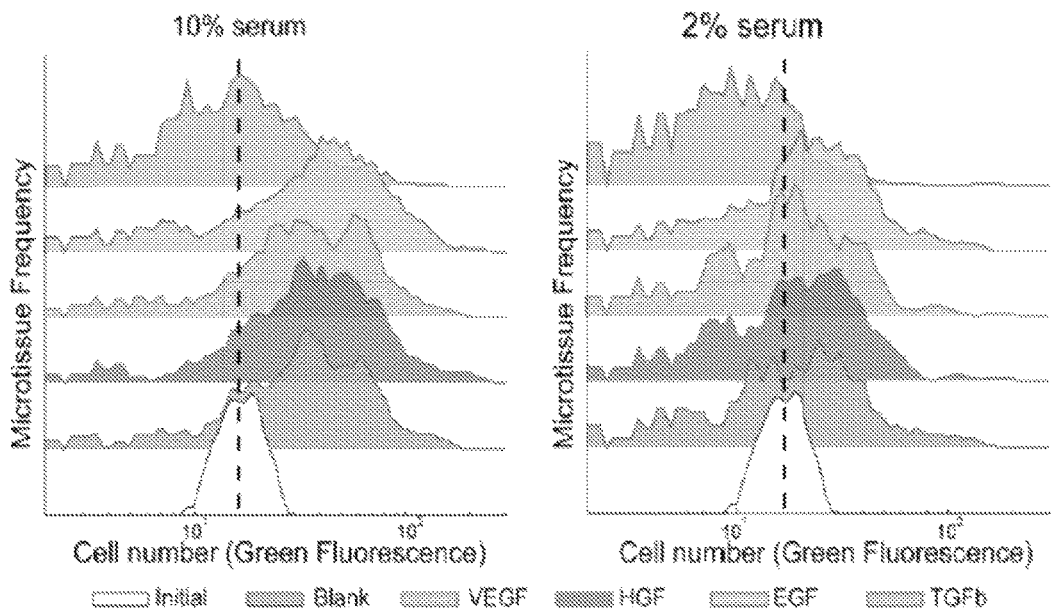
Figure 17A:
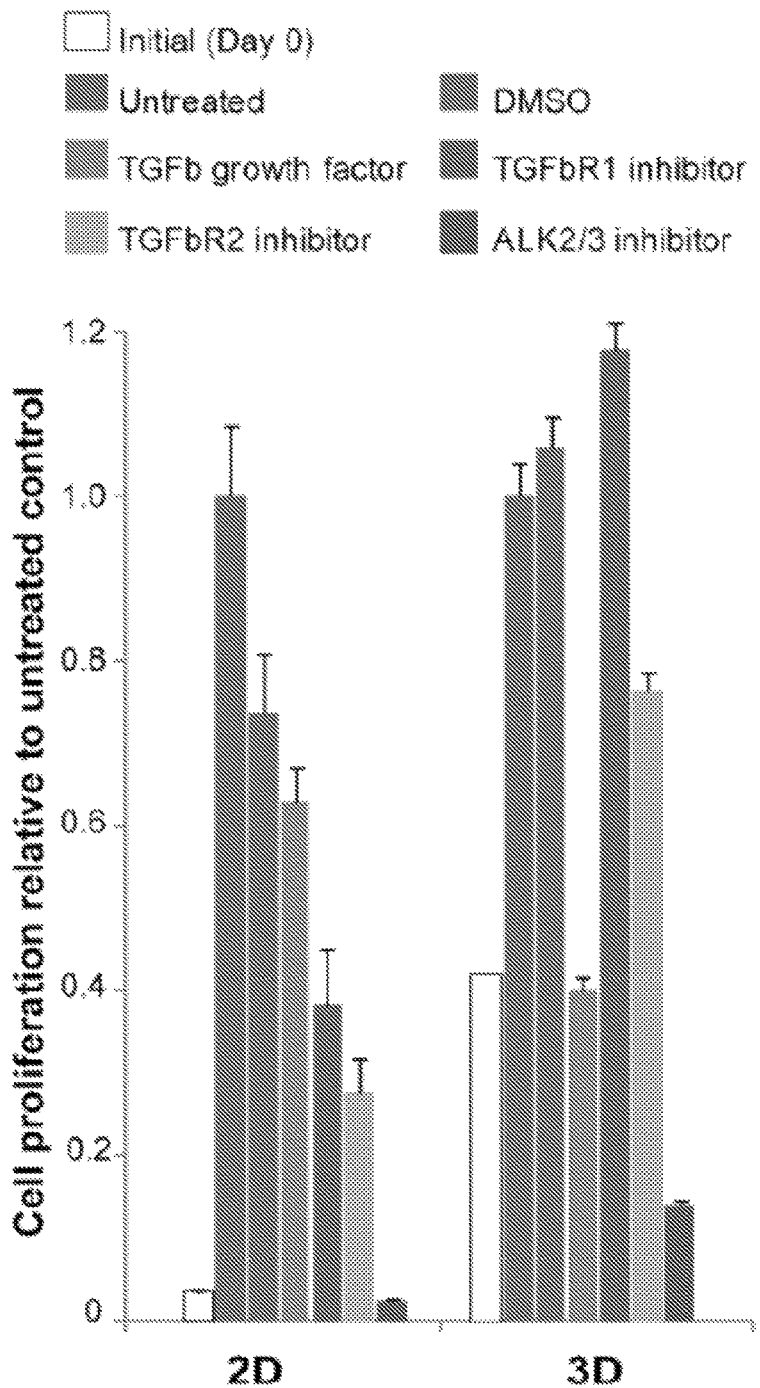
FIG. 17. Differences in tumor cell responses to small molecules in 2D vs. 3D culture. (a) Comparison of proliferation rates on 2D-microplate and 3D-microtissue formats relative to untreated controls. (b) Growth curve over time of tumor cells in 2D measured by microplate fluorescence, and (c) Growth curve over time of tumor cells in 3D measured by gel dissolution and DNA quantitation.
Figure 17B:
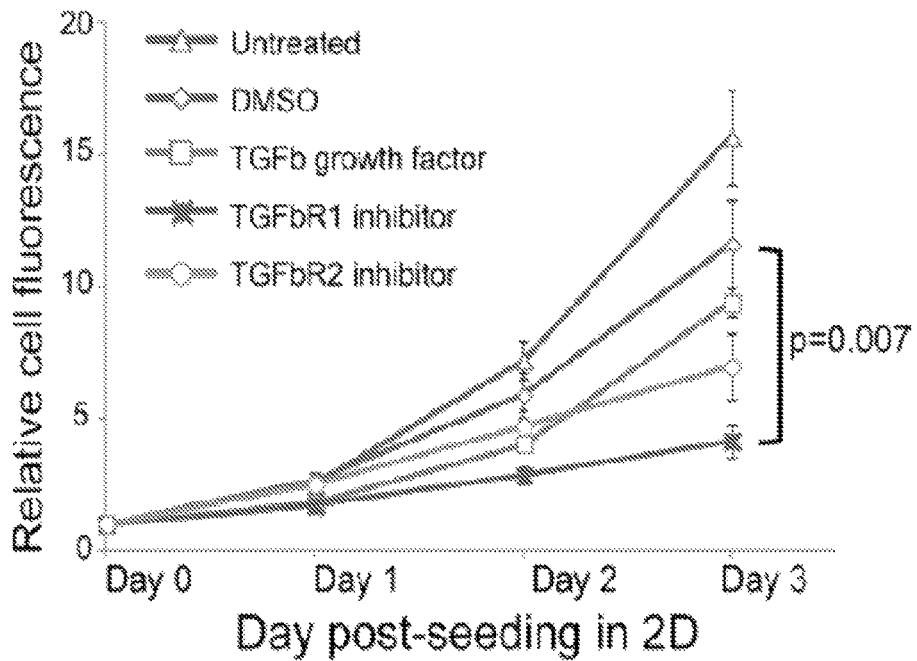
Figure 17C:
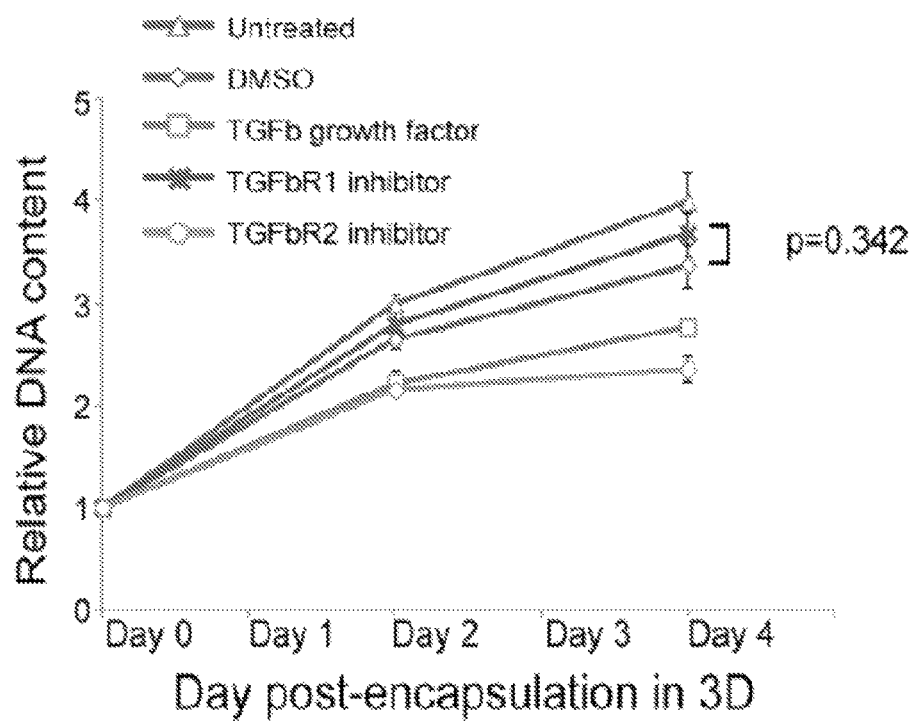

Using this platform, we modulated the 3D proliferation of encapsulated tumor cells by incorporating extracellular (ECM) proteins (fibronectin promoted growth) and exogenous growth factors (TGF-β slows proliferation by ~80%) (FIG. 16). Screening of several small-molecule inhibitors involved in the TGF-β pathway identified a molecule that inhibited tumor cell growth on a 2D microplate but had the opposite effect in 3D (FIG. 17), demonstrating the importance of a 3D model environment in predicting drug responses.

Other Embodiments

It is to be understood that while the invention has been described in conjunction with the detailed description thereof, the foregoing description is intended to illustrate, and not limit the scope of the invention, which is defined by the scope of the appended claims. Other aspects, advantages, and modifications are within the scope of the following claims.

In addition, the contents of all references, patents, and patent applications cited throughout this application are hereby incorporated by reference.

REFERENCES

1. L. G. Griffith and M. A. Swartz, *Nat Rev Mol Cell Biol*, 2006, 7, 211-224.
2. A. Khademhosseini, R. Langer, J. Borenstein and J. P. Vacanti, *Proceedings of the National Academy of Sciences of the United States of America*, 2006, 103, 2480-2487.
3. J. Jung, M. Zheng, M. Goldfarb and K. S. Zaret, *Science*, 1999, 284, 1998-2003.
4. O. Cleaver and D. A. Melton, *Nat Med*, 2003, 9, 661-668.
5. S. N. Bhatia, U. J. Balis, M. L. Yarmush and M. Toner, *FASEB J*, 1999, 13, 1883-1900.
6. S. J. Morrison and A. C. Spradling, *Cell*, 2008, 132, 598-611.
7. N. A. Bhowmick, E. G. Neilson and H. L. Moses, *Nature*, 2004, 432, 332-337.
8. S. L. Friedman, *J Biol Chem*, 2000, 275, 2247-2250.
9. D. Hanahan and R. A. Weinberg, *Cell*, 2011, 144, 646-674.
10. E. E. Hui and S. N. Bhatia, *Proc Natl Acad Sci USA*, 2007, 104, 5722-5726.
11. S. March, E. E. Hui, G. H. Underhill, S. Khetani and S. N. Bhatia, *Hepatology*, 2009, 50, 920-928.
12. D. Huh, B. D. Matthews, A. Mammoto, M. Montoya-Zavala, H. Y. Hsin and D. E. Ingber, *Science*, 2010, 328, 1662-1668.
13. M. A. LaBarge, C. M. Nelson, R. Villadsen, A. Fridriksdottir, J. R. Ruth, M. R. Stampfer, O. W. Petersen and M. J. Bissell, *Integrative Biology*, 2009, 1, 70-79.
14. G. H. Underhill, A. A. Chen, D. R. Albrecht and S. N. Bhatia, *Biomaterials*, 2007, 28, 256-270.
15. K. R. Stevens, K. L. Kreutziger, S. K. Dupras, F. S. Korte, M. Regnier, V. Muskheli, M. B. Nourse, K. Bendixen, H. Reinecke and C. E. Murry, *Proc Natl Acad Sci USA*, 2009, 106, 16568-16573.
16. C. Fischbach, R. Chen, T. Matsumoto, T. Schmelzle, J. S. Brugge, P. J. Polverini and D. J. Mooney, *Nature Methods*, 2007, 4, 855-860.
17. D. R. Albrecht, V. L. Tsang, R. L. Sah and S, N. Bhatia, *Lab Chip*, 2005, 5, 111-118.
18. D. R. Albrecht, G. H. Underhill, T. B. Wassermann, R. L. Sah and S. N. Bhatia, *Nat Methods*, 2006, 3, 369-375.
19. V. Liu Tsang, A. A. Chen, L. M. Cho, K. D. Jadin, R. L. Sah, S. DeLong, J. L. West and S. N. Bhatia, *FASEB J*, 2007, 21, 790-801.
20. V. Chan, P. Zorlutuna, J. H. Jeong, H. Kong and R. Bashir, *Lab on a Chip*, 2010, 10, 2062-2070.
21. W. Tan and T. A. Desai, *Biomaterials*, 2004, 25, 1355-1364.
22. A. P. McGuigan and M. V. Sefton, *Proc Natl Acad Sci USA*, 2006, 103, 11461-11466.
23. Z. J. Gartner and C. R. Bertozzi, *Proc Natl Acad Sci USA*, 2009, 106, 4606-4610.
24. Y. Du, E. Lo, S. A11 and A. Khademhosseini, *Proc Natl Acad Sci USA*, 2008, 105, 9522-9527.
25. B. Guillotin and F. Guillemot, *Trends Biotechnol*, 2011.
26. G. M. Whitesides and B. Grzybowski, *Science*, 2002, 295, 2418-2421.
27. A. A. Chen, G. H. Underhill and S. N. Bhatia, *Integr Biol (Camb)*, 2010, 2, 517-527.
28. D. A. Bruzewicz, A. P. McGuigan and G. M. Whitesides, *Lab Chip*, 2008, 8, 663-671.

29. Y. Du, M. Ghodousi, E. Lo, M. K. Vidula, O. Emiroglu and A. Khademhosseini, *Biotechnol Bioeng,* 2009.
30. A. Khademhosseini and R. Langer, *Biomaterials,* 2007, 28, 5087-5092.
S31. S. Y. Teh, R. Lin, L. H. Hung and A. P. Lee, *Lab on a Chip,* 2008, 8, 198-220.
32. A. Liau, R. Karnik, A. Majumdar and J. H. Cate, *Anal Chem,* 2005, 77, 7618-7625.
33. P. Panda, S. Ali, E. Lo, B. G. Chung, T. A. Hatton, A. Khademhosseini and P. S. Doyle, *Lab Chip,* 2008, 8, 1056-1061.
34. G. M. Cruise, D. S. Scharp and J. A. Hubbell, *Biomaterials,* 1998, 19, 1287-1294.
35. R. Novak, Y. Zeng, J. Shuga, G. Venugopalan, D. A. Fletcher, M. T. Smith and R. A. Mathies, *Angewandte Chemie-International Edition,* 2011, 50, 390-395.
36. L. F. Yu, M. C. W. Chen and K. C. Cheung, *Lab on a Chip,* 2010, 10, 2424-2432.
37. E. Jabbari, *Curr Opin Biotechnol,* 2011.
38. D. J. Quick and K. S. Anseth, *J Control Release,* 2004, 96, 341-351.
39. D. C. Pregibon, M. Toner and P. S. Doyle, *Science,* 2007, 315, 1393-1396.
40. G. T. Hermanson, *Bioconjugate techniques,* Academic Press, San Diego, 1996.
41. Z. J. Gartner and D. R. Liu, *J Am Chem Soc,* 2001, 123, 6961-6963.
42. C. A. Mirkin, R. L. Letsinger, R. C. Mucic and J. J. Storhoff, *Nature,* 1996, 382, 607-609.
43. G. A. Kwong, C. G. Radu, K. Hwang, C. J. Shu, C. Ma, R. C. Koya, B. Comin-Anduix, S. R. Hadrup, R. C. Bailey, O. N. Witte, T. N. Schumacher, A. Ribas and J. R. Heath, *J Am Chem Soc,* 2009, 131, 9695-9703.
44. E. S. Douglas, R. A. Chandra, C. R. Bertozzi, R. A. Mathies and M. B. Francis, *Lab Chip,* 2007, 7, 1442-1448.
45. M. P. Valignat, O. Theodoly, J. C. Crocker, W. B. Russel and P. M. Chaikin, *Proc Natl Acad Sci USA,* 2005, 102, 4225-4229.
46. D. Nykypanchuk, M. M. Maye, D. van der Lelie and O. Gang, *Nature,* 2008, 451, 549-552.
47. G. M. Whitesides and M. Boncheva, *Proc Natl Acad Sci USA,* 2002, 99, 4769-4774.
48. D. Dendukuri, P. Panda, R. Haghgooie, J. M. Kim, T. A. Hatton and P. S. Doyle, *Macromolecules,* 2008, 41, 8547-8556.
49. R. C. Fry, J. P. Svensson, C. Valiathan, E. Wang, B. J. Hogan, S. Bhattacharya, J. M. Bugni, C. A. Whittaker and L. D. Samson, *Genes & Development,* 2008, 22, 2621-2626.
50. S. J. Bryant, C. R. Nuttelman and K. S. Anseth, *Journal of Biomaterials Science-Polymer Edition,* 2000, 11, 439-457.

We claim:

1. A method of making a plurality of microtissues, comprising injecting into a channel of a microfluidic device a first input stream comprising a solution of cells and a second input stream comprising a polymerizable hydrogel solution to form a combined aqueous stream;

emulsifying the combined aqueous stream with an oil stream in a first region of the channel of the microfluidic device, to produce droplets comprising the cells in the polymerizable hydrogel;

mixing said droplets to disperse the cells in the polymerizable hydrogel in a second region of the channel comprising a corrugated section in the microfluidic device;

polymerizing the droplets comprising the cells dispersed in the polymerizable hydrogel to form the microtissues; and collecting the microtissues from an outlet of the device, such that the plurality of microtissues is made.

2. The method of claim 1, wherein the hydrogel material is agarose, fibrin, or polyethylene hydrogel.

3. A method of making a plurality of microtissues, comprising injecting into a channel of a microfluidic device a solution comprising pre-stabilized, micropatterned cell clusters and a polymerizable hydrogel solution, wherein the cell clusters comprise parenchymal cells and supporting non-parenchymal cells;

emulsifying the solution of cell clusters and polymerizable hydrogel with an oil stream in a channel of the microfluidic device, to produce droplets comprising the cell clusters in the polymerizable hydrogel, polymerizing the droplets comprising the cell clusters dispersed in the polymerizable hydrogel to form the microtissues, wherein polymerizing occurs during transport of the droplets, wherein transport occurs continuously; and collecting the microtissues from an outlet of the device, such that the plurality of microtissues is made.

4. The method of claim 3, wherein the cell clusters comprise primary hepatocytes and stromal cells.

5. The method of claim 3, wherein the cell clusters comprise hepatocytes selected from the group consisting of progenitor-derived hepatocytes, ES-derived hepatocytes, and induced pluripotent stem cell-derived (iPS-derived) hepatocytes, and stromal cells.

6. The method of claim 3, wherein the cell clusters comprise cancer cells and stromal cells.

7. The method of claim 1 or 3, wherein the polymerizable hydrogel is a photopolymerizable hydrogel.

8. The method of any one of claims 1-4, wherein the hydrogel is functionalized with one or more affinity biomolecules facilitating higher ordered assembly of the said microtissues.

9. The method of claim 8, wherein the biomolecule is streptavidin, or a cell adhesive peptide.

10. The method of claim 3, wherein the droplets or microtissues are about 50 to about 250 μM in diameter.

11. The method of claim 1 or 3, wherein the droplets or microtissues are about 20 to about 150 μM in diameter.

12. The method of claim 1 or 3, wherein the droplets comprise about 1 to about 50 cells.

13. The method of claim 1 or 3, wherein each microtissue comprises about 2 to about 20 cells or wherein each microtissue comprises about 5 to about 10 cells.

14. The method of claim 4, wherein the stromal cells are fibroblasts.

15. The method of claim 5, wherein the stromal cells are fibroblasts.

16. The method of claim 6, wherein the stromal cells are fibroblasts.

17. The method of claim 7, wherein the photopolymerziable hydrogel is polyethylene glycol (PEG) hydrogel.

18. The method of claim 9, wherein the biomolecule is a RGDS peptide.

* * * * *

UNITED STATES PATENT AND TRADEMARK OFFICE
CERTIFICATE OF CORRECTION

PATENT NO. : 10,260,039 B2  
APPLICATION NO. : 14/116901  
DATED : April 16, 2019  
INVENTOR(S) : Sangeeta N. Bhatia et al.

Page 1 of 1

It is certified that error appears in the above-identified patent and that said Letters Patent is hereby corrected as shown below:

In the Specification

At Column 1, Line 16, replace "This invention was made with government support under grant nos. ROI-DK56966 6914791 and ROI-EB008396 6920502, awarded by the National Institutes of Health (NIDDK). The government has certain rights in the invention."" with --"This invention was made with government support under DK056966 and EB008396 awarded by the National Institutes of Health. The government has certain rights in the invention."--

Signed and Sealed this  
Ninth Day of April, 2024

Katherine Kelly Vidal  
*Director of the United States Patent and Trademark Office*